US005487378A

United States Patent [19]
Robertson et al.

[11] Patent Number: 5,487,378
[45] Date of Patent: Jan. 30, 1996

[54] INHALER

[75] Inventors: Paul A. Robertson, Chishall; Peter J. Houzego, Oakington, both of Great Britain; Borge R. Jensen, Brussels, Belgium; Murray A. Creeke, Saffron Walden, Great Britain; Neil Emerton, Riverside, Great Britain; Peter D. Hodson, Trowell, Great Britain; Eric A. Baum, Loughborough, Great Britain

[73] Assignee: Minnesota Mining and Manufacturing Company, St. Paul, Minn.

[21] Appl. No.: 78,151

[22] PCT Filed: Dec. 17, 1991

[86] PCT No.: PCT/GB91/02250

§ 371 Date: Oct. 4, 1993

§ 102(e) Date: Oct. 4, 1993

[87] PCT Pub. No.: WO92/11050

PCT Pub. Date: Jul. 9, 1992

[30] Foreign Application Priority Data

Dec. 17, 1990 [GB] United Kingdom .................... 9027257
Jan. 24, 1991 [GB] United Kingdom .................... 9101527

[51] Int. Cl.$^6$ ................................................. A61M 11/00
[52] U.S. Cl. ................................ 128/200.16; 128/200.14; 128/204.23
[58] Field of Search ........................ 128/200.14, 200.16, 128/203.12, 203.15, 203.21, 204.23

[56] References Cited

U.S. PATENT DOCUMENTS

| | | | |
|---|---|---|---|
| 3,593,712 | 7/1971 | Weaver | 128/200.16 |
| 3,605,741 | 9/1971 | Spencer | 73/861.05 |
| 3,662,598 | 5/1972 | Spencer | 73/861.05 |
| 3,812,854 | 5/1974 | Michaels et al. | 128/194 |
| 4,051,723 | 10/1977 | Head et al. | 73/861.05 |
| 4,159,803 | 7/1979 | Cameto et al. | 239/102 |
| 4,294,407 | 10/1981 | Reichl et al. | 128/200.16 |
| 4,300,546 | 11/1981 | Kruber | 128/200.16 |
| 4,334,531 | 6/1982 | Reichl et al. | 128/200.14 |
| 4,338,576 | 7/1982 | Takahashi et al. | 331/67 |
| 4,465,234 | 8/1984 | Maehara et al. | 239/102 |
| 4,512,187 | 4/1985 | Sigwardt | 73/198 |
| 4,533,082 | 8/1985 | Maehara et al. | 239/102 |

(List continued on next page.)

FOREIGN PATENT DOCUMENTS

| | | |
|---|---|---|
| 0257590A2 | 3/1988 | European Pat. Off. . |
| 0482814A1 | 4/1992 | European Pat. Off. . |
| 2476306 | 8/1981 | France . |
| 945195 | 12/1963 | United Kingdom . |
| 1250451 | 10/1971 | United Kingdom . |
| 1432741 | 4/1976 | United Kingdom . |
| 1591881 | 7/1981 | United Kingdom . |
| 2089767 | 6/1982 | United Kingdom . |
| 2126193 | 3/1984 | United Kingdom . |
| 2203492 | 10/1988 | United Kingdom . |
| 2233084 | 1/1991 | United Kingdom . |
| 2240494 | 6/1991 | United Kingdom . |
| WO86/03290 | 6/1986 | WIPO . |
| 89/06147 | 7/1989 | WIPO . |
| WO90/10197 | 9/1990 | WIPO . |

Primary Examiner—Aaron J. Lewis
Attorney, Agent, or Firm—Gary L. Griswold; Walter N. Kim; Dale E. Hulse

[57] ABSTRACT

An inhaler for dispensing droplets of liquid medicament to a patient comprising a body having a mouthpiece or nasal adaptor and a reservoir of liquid medicament in communication with an aerosol generator. The aerosol generator includes a chamber for the liquid medicament and a nozzle arrangement having a plurality of orifices. Means are provided for cyclically pressurizing the liquid medicament in the chamber such that liquid from the chamber is periodically expelled through the orifices of the nozzle arrangement as atomizer droplets of liquid medicament. Dosage control means are also provided for deactivating the aerosol generator after a predetermined time or after a predetermined volume of liquid medicament has been expelled from the chamber.

24 Claims, 14 Drawing Sheets

U.S. PATENT DOCUMENTS

| | | | |
|---|---|---|---|
| 4,632,311 | 12/1986 | Nakane et al. | 239/101 |
| 4,781,066 | 11/1988 | Pope et al. | 73/239 |
| 4,850,534 | 7/1989 | Takahashi et al. | 239/102.2 |
| 5,063,922 | 11/1991 | Häkkinen | 128/200.16 |
| 5,134,993 | 8/1992 | van der Linden et al. | 128/200.16 |
| 5,152,456 | 10/1992 | Ross et al. | 239/102.2 |
| 5,261,601 | 11/1993 | Ross et al. | 239/102.2 |
| 5,302,093 | 4/1994 | Owens et al. | 417/474 |
| 5,331,953 | 7/1994 | Andersson et al. | 128/200.14 |

FIG. 1a

1 LIQUID RESERVOIR → FLOW GAUGE → AEROSOL GENERATOR 3
5 BREATH ACTUATION SENSOR → ELECTRONICS 4

FIG. 1b

6 LIQUID RESERVOIR → AEROSOL GENERATION 7
9 BREATH SENSOR → ELECTRONICS 8

FIG. 2

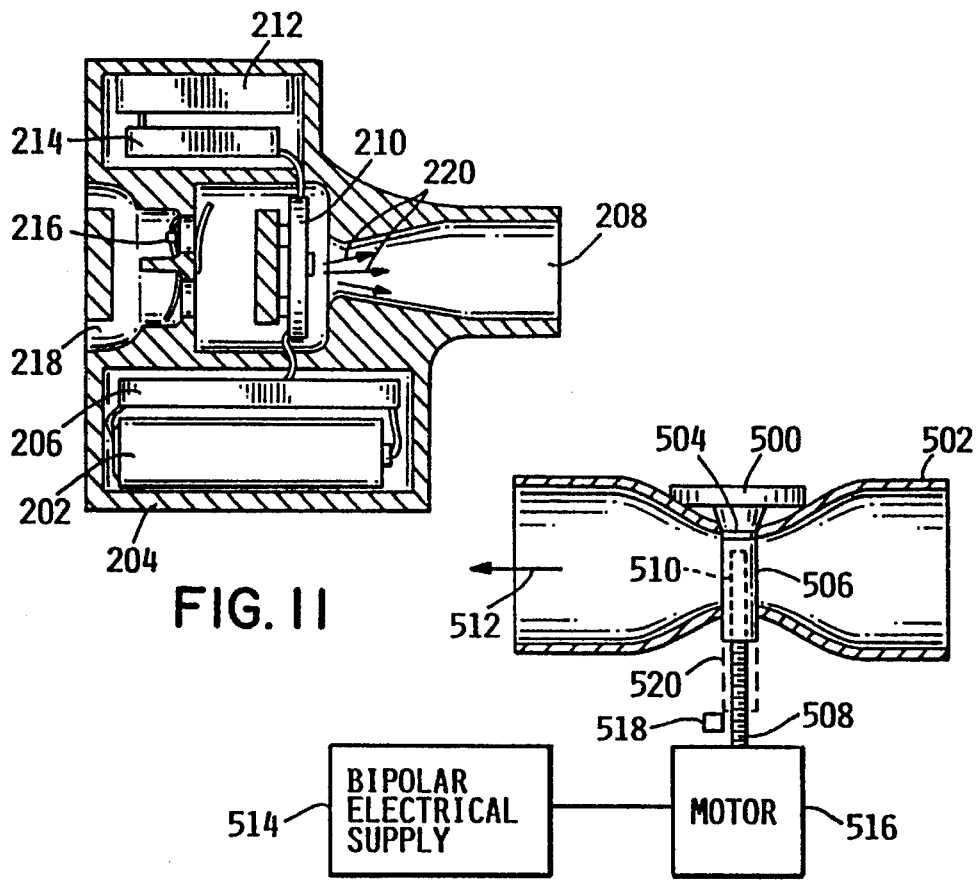
FIG. 11
FIG. 12
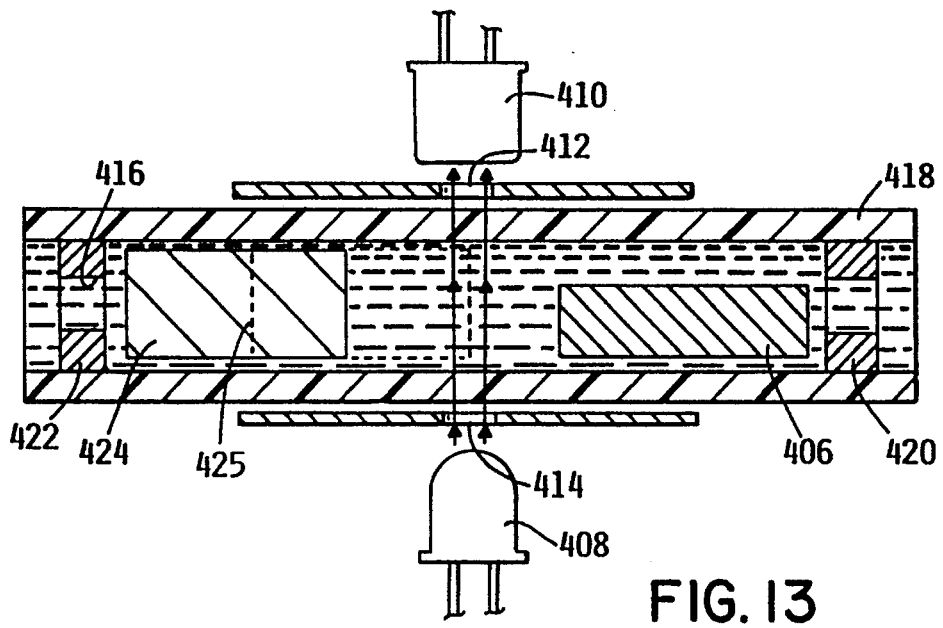
FIG. 13

INHALER

FIELD OF THE INVENTION

This invention relates to inhalers for the delivery of therapeutic substances to the respiratory system of a patient and in particular to inhalers which deliver the therapeutic substance in the form of a liquid as a dispersion of fine droplets.

BACKGROUND

Since the metered dose pressurised inhaler was introduced in the mid-1950's, inhalation has become the most widely used route for delivering bronchodilators, offering a rapid onset of action and a low instance of systemic side effects. More recently, inhalation from a pressurised inhaler has been a route selected for the administration of other drugs, e.g., ergotamine, which are not primarily concerned with the treatment of a bronchial malady.

The metered dose inhaler is dependent upon the propulsive force of a propellant system used in its manufacture. The propellant generally comprises a mixture of liquified chlorofluorocarbons (CFC's) which are selected to provide the desired vapour pressure and stability of the formulation. Propellants 11, 12 and 114 are the most widely used propellants in aerosol formulations for inhalation administration.

In recent years it has been established that CFC's react with the ozone layer around the earth and contribute towards its depletion. There has been considerable pressure around the world to reduce substantially the use of CFC's, and various Governments have banned the "non-essential" use of CFC's. Such "non-essential" uses include the use of CFC's as refrigerants and blowing agents, but heretofore the use of CFC's in medicines, which contributes to less than 1% of the total use of CFC's, has not been restricted. Nevertheless, in view of the adverse effect of CFC's on the ozone layer it is desirable to seek alternative propellant systems which are suitable for use in inhalation aerosols or an inhaler which is capable of delivering drugs in such an efficacious manner without employing an aerosol propellant.

Apparatus for atomising liquid, such as, liquid fuel, water, liquid drug and recording medium are disclosed, for example, in U.S. Pat. Nos. 3,812,854, 4,159,803, 4,300,546, 4,334,531, 4,465,234, 4,632,311, 4,338,576 and 4,850,534 and International Patent Application No. WO/8906147.

The atomising apparatus disclosed in U.S. Pat. Nos. 4,465,234 and 4,632,311 comprises a body having a chamber into which liquid is supplied, a nozzle member secured to the body and forming part of a wall defining the chamber, the nozzle member having at least one nozzle opening therethrough, and vibrator which is either a separate element forming part of a wall defining the chamber or is secured to the nozzle member to cause vibration thereof, such that, in use, in response to the vibrator, liquid in the chamber is cyclically pressurised, causing liquid to be periodically expelled through the nozzle opening(s) as atomised droplets. The apparatus additionally comprises a reservoir of liquid positioned below the chamber and a suction pump in communication with the chamber via an air vent pipe for sucking liquid into the chamber. The pump is de-energised after operation to drain liquid to leave the chamber dry during non-working periods to prevent the otherwise solid substances from clogging the nozzle openings.

U.S. Pat. No. 4,533,082 discloses an arrangement for discharging liquid droplets which is useful in applications such as fuel burners and printers, the arrangement comprises a housing including a chamber for holding liquid therein having an intake port connected to a liquid supply container, a vibrating member secured to the housing in pressure transmitting relation with the liquid in the chamber. The vibrating member is formed with at least one nozzle opening therein through which the liquid is discharged forwardly of the housing. A piezo-electric transducer is secured to the vibrating member for inducing a rearward displacement therein to discharge a small quantity of liquid through the nozzle opening.

U.S. Pat. Nos. 4,338,576 and 4,850,534 disclose a nebuliser which pumps up water and mists the pumped up water comprising an elongated main body with a centre hole for water passage, and piezoelectric vibration elements together with electrodes for energising the same mounted on the main body. The vibration elements are water-proofed, with the nebuliser itself supported by a flange on a water-proof member, which flange is on a plane on which a centre electrode is positioned. Upon vibration of the elements, water is pumped up through the inlet of the main body and dissipated into the air through the outlet of the main body. Preferably, the inlet and the outlet are removable from the main body and the inlet coated with a thin hard film. The outlet is preferably covered with a mesh, or at least an opening of the outlet is covered, for preventing the release of water that has not been converted to mist.

British Patent Application No. 2240494A, published 7th Aug., 1991, discloses a dispensing apparatus comprising a housing defining a chamber receiving in use a quantity of liquid to be dispensed, the housing comprising a perforate membrane which defines a front wall of the chamber and which has a rear face contacted by liquid in use, the apparatus further comprising vibrating means connected to the housing and operable to vibrate the perforate membrane to dispense droplets of liquid through the perforate membrane, wherein the housing comprises an annular member having a relatively thin inner annular portion connected to the perforate membrane and a relatively thick outer annular portion connected to the vibrating means.

SUMMARY OF THE INVENTION

The present invention provides an inhaler capable of dispensing doses of a liquid medicament in the form of atomised droplets.

According to the present invention there is provided an inhaler device for dispensing droplets of liquid medicament to a patient comprising a body having a mouth piece or nasal adaptor, and a reservoir of liquid medicament in communication with an aerosol generator, the aerosol generator comprising a chamber for liquid medicament and a nozzle arrangement comprising a plurality of orifices in fluid flow relationship with liquid medicament in said chamber, means for cyclically pressurising the liquid medicament in said chamber such that liquid from said chamber is periodically expelled through the orifices as atomised droplets of liquid medicament so they may be inhaled via the mouth piece or nasal adaptor, the inhaler additionally comprising dosage control means for deactivating the aerosol generator after a predetermined time or after a predetermined volume of liquid medicament has been expelled from the chamber.

The inhaler of the invention is capable of dispensing accurate doses of liquid medicament in the form of atomised droplets of size suitable for inhalation therapy. The inhaler may be constructed in the form of a small battery powered, portable device, e.g., pocket sized, capable of being used to dispense metered doses of liquid drugs, as a replacement for conventional pressurised aerosol inhalers. The term "liquid drugs" includes drugs in solution form, e.g., in aqueous solution, ethanolic solution, aqueous/ethanolic mixture solution, etc. and in colloidal suspension form.

In a preferred embodiment of the invention the inhaler comprises means to detect a patient's inspiration associated with a triggering means in order that the inhaler may be automatically triggered at the correct point of a patient's breathing cycle thereby avoiding the need for the patient to co-ordinate inspiration with operation of the inhaler.

The aerosol generator used in the inhaler of the invention comprises a chamber for liquid medicament and a nozzle arrangement comprising a plurality of orifices in fluid flow relationship with the liquid in the chamber. The orifices typically have a maximum opening in the range 2 to 50 µm (microns) and produce atomised droplets having a size comparable to the diameter. For medicament intended to reach the alveoli of the lungs, the apertures desirably have a maximum opening of from 2 to 10 µm (microns), preferably below 5 µm (microns), in order to produce atomised droplets within that range. For liquid medicament intended to be administered to the nasal passage, mouth, throat or other parts of the respiratory system, the larger orifices may be employed. The orifices may have the same or different diameters. Preferably, the orifices are tapered towards the intended outlet for the liquid. The orifices are generally spaced from each other by distances within the range 20 to 200 microns. The nozzles may be fabricated by the same technique to manufacture microsieves, e.g., electro forming in nickel. Alternatively, the nozzle arrangement may be formed by patterned anisotropic etching through a thin semiconductor wafer, e.g., of silicon or germanium. Alternatively, plastics nozzle arrays may be used.

The thickness of the nozzle arrangement is typically in the range 20 to 100 µm (microns).

A preferred nozzle array comprises an electroformed nickel foil about 10 µm thick with holes approximately 6 µm in diameter set on a 50 µm pitch. A reinforcing grid of about 60 µm thickness is electroformed over the thinner foil for additional strength. Such foils are commercially available from Stork-Veco BV of Holland and have been sold for use as microsieves.

The aerosol generator is constructed to cyclically pressurise liquid in the chamber causing the liquid periodically to be expelled through the orifices as atomised droplets of liquid. The cyclic pressurisation may be achieved utilising a piezo-electric element which is caused to vibrate ultrasonically and acts directly or indirectly on the liquid.

In one embodiment of the invention the chamber of the aerosol generator comprises a flexible disc forming or in contact with at least part of a wall of the chamber, the flexible disc being attached to a piezoelectric element, to form a vibrator element. The vibrator element is excited by a suitable resonant frequency typically in the ultrasonic range of 50 to 250 kHz, although the range 10 kHz to 500 kHz may be employed. Ultrasonic pressure waves propagate through the disc, cavity walls and liquid, resulting in liquid being forced periodically at ultrasonic frequencies through the nozzles. The use of a resonant mode above the fundamental mode frequency enables low drive voltages and power to achieve high liquid ejection flow rates through the nozzle arrangement. The flexible vibrator element may conveniently be positioned in a wall opposite to the nozzle arrangement, although this configuration is not essential and the vibrator element may be in any position which will propogate a pressure wave within the liquid causing droplets to be expelled through the nozzle arrangement.

Suitable vibrator elements are commercially available from Kyocera and Murata of Japan and have been sold for use as piezo acoustic buzzer elements. The elements are brass 20 mm in diameter bonded to a 14 mm diameter piezo electric disc. The brass disc may be polished and electroplated with nickel to give a corrosion resistant finish.

The material forming the remaining cavity walls of the aerosol generator has been found to give best results if it is a relatively low acoustic loss and impedance material. For example, aluminium alloy, Perspex, polycarbonate and ABS plastic have been found to work well, whereas nickel and stainless steel are not so effective.

One advantage of ABS is that it may be injection moulded to form a complete assembly. In this case the aerosol generator disc may be linked to the body of the device by a 'limb' which contains the liquid feed channel.

The adhesive bonding between the vibrator element and the cavity walls is also important. Two part epoxy resins, e.g., Araldite commercially available from Ciba-Geigy in the United Kingdom, work well whereas silicone rubber does not, suggesting that good acoustic coupling between the components is desirable. The nozzle array may also be conveniently bonded with epoxy resin. Hot melt adhesives may also be employed.

In an alternative embodiment of the invention the nozzle assembly is vibrated. The nozzle assembly may be flexible and comprise a piezo-electric element, e.g., in the form of a ring attached to the nozzle array extended around the orifices, such that when the piezo-electric element is excited it causes vibration of the nozzle arrangement at ultrasonic frequencies resulting in cyclic pressurisation of the liquid in the chamber and ejection of droplets of liquid through the orifices.

In a preferred embodiment the nozzle assembly is vibrated by a vibrator element comprising a piezo-electric ring secured to a metal disc of larger diameter, the vibrating element having a central aperture through which droplets from the nozzle array are emitted. The vibrating element is preferably secured only over its central portion, either directly to the nozzle array or to the housing of the chamber in close proximity to the nozzle array e.g. over a central portion of about 4 mm diameter, such that ultrasonic energy is transferred directly to the nozzle array. This arrangement allows the outer area of the vibrating element, which is typically about 20 mm diameter, to vibrate freely as a resonator and enables aerosol generation to occur with an input power to the piezo-electric element of about 0.5 W. Also the arrangement has less tendency to draw tiny air bubbles in through the nozzles during operation, since this reduces the tendency for and effects of, vibrational mode hopping which can occur if the piezo driver is attached around its periphery.

The drive frequency for this arrangement is still typically in the range 250 to 400 kHz where the vibrating element operates in an overtone mode with a complex mode pattern. It is likely that this frequency corresponds to the radial mode of the piezo which in turn excites other modes in the metal element. The use of overtone frequencies of the metal element i.e. those above the fundamental allows thin, low cost pieces of piezo to be employed. Generally, the thickness of the piezo element and the metal disc should be similar. Hence if the metal thickness were increased to raise the fundamental resonant frequency of the vibrating element a thicker piezo element, and therefore of higher cost, would also be required.

The overall dimension of the aerosol generator may be small, e.g., 20 millimeters in diameter and 3 millimeters thick and is capable of delivering volumes of several microliters of atomised droplets of liquid in a time period of about 0.5 seconds.

The chamber of the aerosol generator is supplied with liquid medicament from a reservoir. It has been found that the presence of air in the chamber or liquid, even in the form of minute bubbles may deleteriously effect the performance of the aerosol generator, particularly if air bubbles are present in the region of the nozzle arrangement. This effect is less marked with the arrangement where the vibrator element is attached directly to the nozzle array or to the housing in close proximity to the nozzle array. The reservoir may be arranged to supply liquid to the chamber only when the inhaler is used, although in practice it has been found that it is difficult to repeatedly fill and empty the chamber of the aerosol generator without entrapping air bubbles during the filling. Accordingly, it is preferred that the chamber is permanently filled with liquid. In order to avoid the problem of liquid leaking from the chamber via the nozzle arrangement during the time when the inhaler is not in use, e.g., storage in a pocket, the nozzle arrangement may be conveniently sealed with a cap.

Also, it is desirable for the reservoir to supply the chamber at a slight negative head of pressure regardless of the reservoir orientation. This effect may be achieved by employing a liquid reservoir in the form of a collapsible bag or sachet having a feed tube connecting with the chamber sealed within the bag. The bag may conveniently be constructed of latex rubber, polyester or other polymer materials or composite materials such as a metalised polymer laminate. The structure of the bag or sachet is such that it has some stiffness giving a tendency to expand to a state of maximum internal volume. This may be accomplished by the natural stiffness of the bag walls, by internal expansion means, e.g., a spring or compressed foam insert within the bag or by positioning the bag in a container containing a gas at a pressure less than atmospheric pressure. The container may be conveniently in the form of a metal can or other impermeable material which will also serve to reduce evaporation losses of liquid. The container may be vented to atmosphere periodically in use to prevent an excessive negative pressure from building up in the reservoir as the liquid is dispensed.

The inhaler device of the invention additionally comprises dosage control means such that the inhaler will be deactivated after a predetermined time or after a predetermined volume of liquid has been dispensed. The dosage control means preferably comprises means for measuring the volume of liquid supplied to the chamber and means to generate a signal after a predetermined volume of liquid has been supplied, which signal is used to deactivate the aerosol generator. Alternatively, the dosage control may comprise a timer which allows actuation of the aerosol generator for a predetermined period and thereafter causes deactivation.

The dosage control means may conveniently be positioned to measure the volume of liquid passing through a section of a conduit connecting the chamber of the aerosol generator to the reservoir. In one embodiment of the invention the dosage control means comprises a length of tube inside which a close fitting, free moving slug is located. The net density of the slug is approximately matched to that of the liquid which flows through the bore of the tube, i.e. the slug has neutral buoyancy. The position of the slug inside the tube is monitored by optical, electrical, magnetic, capacitive or electromagnetic or other such means. At the start and/or end of the liquid dose measurement period the slug is set to a predetermined or measured position, for example, by means of a push-rod or another slug or by magnetic attraction pushing or pulling the slug itself against an end stop. The aerosol generator is then activated and liquid is drawn through the gauge. As the liquid moves along the gauge, the slug is drawn along with it until it reaches a predetermined end point whereupon the aerosol generator is de-activated and the liquid flow stops. The slug may then be reset to its start position by the means described previously. The clearance between the slug and the tube bore is such that the slug both moves along with the liquid flow and may be reset in position by an external force with no net liquid flow as the liquid may flow around the slug as it is returned to its starting position. The liquid gauge may be modified to give a continuous reading of volume dispensed as well as providing a dose completed output by continuously detecting the position of the slug. Examples of such liquid gauges are disclosed in our copending British Patent Application No. 9027256.8.

Bubbles inside the system can present a very serious problem since they can prevent operation of the aerosol generator and/or dose gauge. Hence the bubble free filling and maintenance of a bubble free system is of paramount importance. To reduce the effects of the liquid outgassing to form bubbles during the service life of the device a portion of the liquid feed system may be formed with a gas remover. An area of some part of the liquid feed system is made from microporous material, capable of allowing the passage of gas but not of liquids. Such materials are commercially available, e.g., from 3M, and are typically polymers such as polypropylene or high density polyethylene containing a network of pores of typical diameter<1 μm. The area of such material in contact with the liquid is generally at a point along the feed tubing between the reservoir and aerosol generator. It may even be part of the wall of the feed tubing. On the other side of the microporous material to the drug solution is a sealed space with an internal vacuum or reduced air pressure. The gas remover works by simply causing any small air bubbles to pass through the microporous membrane material into the region of vacuum or low pressure, thus allowing a supply of liquid to the cavity without the risk of air bubble incorporation. This provides a positive means of removing air bubbles before they can reach the delivery cavity of such a device and upset its operation. This provides an extra degree of insurance against such air bubble originated problems under all operating conditions. Because the hydraulic pressures in the liquid feed system are unaltered by the presence of this gas remover and remain constant, then the operation of the device is not compromised in any way. The capacity of the gas remover can be chosen for any desired level of bubble removal ability, completely independently of the reservoir, feed system and cavity volumes.

Air bubbles may enter the aerosol generator through the orifices of the nozzle arrangement when the device is not in use. Subsequent operation of the device does not always dislodge such air bubbles and may deleteriously affect the performance. Accordingly, the device preferably includes a cover or cap to seal the nozzle arrangement to prevent the ingress of air when the device is not in use. In a preferred embodiment the cover has a self-closing action which seals the nozzle arrangement when the patient ceases to inspire through the mouthpiece after delivery of a dose of medicament or when the device is released by the patient. The self-closing action may be achieved by mechanical, e.g., spring, electromechanical, pneumatic or hydraulic means. Our copending British Patent Application No. 9027255.0 "Closure system for inhalers" discloses suitable cover systems for use in the invention.

In addition, or as an alternative, the cover for the nozzle arrangement may be provided with a gas permeable membrane which can be sealed against the nozzle array outer surface and may have a partial vacuum generated by a manual pump, e.g., a rubber bulb, to remove any air bubbles from behind the nozzle arrangement.

The inhaler preferably includes a breath actuation sensor for detecting a patient's inspiration, which sensor provides a signal for actuating the aerosol generator. Thus, a patient simply breathes through the mouth piece or nasal adaptor of the inhaler, the breath actuation sensor will detect the patient's inspiration causing the aerosol generator to emit atomised droplets of liquid medicament which are entrained in the patient's inspiratory air flow. The aerosol generator will be deactivated by dosage control means as soon as the required dose of medicament has been dispensed. It is readily possible to dispense effective doses of liquid medicament during a single inhalation.

The breath actuation sensor may be a mechanical device, for example, a pivoted vane, which moves to close a switch when there is an air flow through the mouth piece. Alternatively, the air flow may be detected by a flow transducer, pressure differential transducer or temperature sensor which detects the cooling effect of an air flow, to provide a signal to trigger actuation of the aerosol generator. The breath actuation sensor may conveniently be positioned in a passage or chamber between an air inlet of the inhaler and the mouth piece or nasal adaptor. The breath actuation sensor may be associated with one or more flap valves in order to prevent air flow over the sensor should the patient exhale through the mouth piece or nasal adaptor.

The inhaler is preferably constructed such that when the patient breathes through the mouthpiece air flowing through the inhaler and the droplets emitted from the aerosol generator are thoroughly mixed as soon as possible after the droplets have left the nozzles if droplet collisions and formation of large droplets are to be minimised. The droplets are emitted at around 10 m/s from each nozzle, and follow each other along a droplet 'streamline'. At an operating frequency of 150 kHz, the axial spacing of the droplets is around 65 µm. If the droplets were to be ejected into still air then the droplet streamlines would slow down and the droplets would all touch at around 1 to 2 m/s. For this inhaler application the droplet size is important to maximise efficacy and hence collisions should be avoided. Therefore the droplets are best injected into a fast moving air stream flowing at right angles to the droplet ejection velocity. This may be achieved by siting the nozzle array at the constriction of a venturi with the air flowing over the top of the nozzles. In this way the droplets may be rapidly and effectively dispersed in the flowing air. Typical minimum air flows required are from 20 to 30 liters/min. through a venturi which varies between 20 mm inlet and outlet diameters to a 10 mm constriction diameter over a few centimeters.

The complete inhaler system preferably comprises two main parts, a replaceable cartridge and a re-usable hand unit.

The replaceable cartridge contains the drug solution and all components which come into contact with it i.e. liquid dose gauge, reservoir sachet, aerosol generator cavity, nozzle array etc. The nozzle cap may be retained on the cartridge or may be present on the hand unit. The cartridge is relatively low cost and disposable.

The re-usable hand unit accepts the cartridge and contains the mechanical and electronic components necessary for generation. For example, the automatic capping system which comprises a small electric motor and leadscrew driving the cap carrier, with associated optical sensors to monitor the cap position and motor rotations may be retained in the hand unit. The venturi to condition the airflow and mix it with the droplets may also be retained in the hand unit with a thermistor to sense air flow rate at its intake. In addition, the hand unit contains one or more batteries to power the system together with the main electronics and switches.

BRIEF DESCRIPTION OF THE DRAWINGS

The invention will now be described with reference to the accompanying drawings in which:

FIGS. 1a and 1b are block diagrams of an inhaler of the invention,

FIG. 2 is a cross-section diagram showing a liquid reservoir, suitable for use in an inhaler of the invention, FIG. 11 represents a schematic diagram of an inhaler in accordance with the invention.

FIG. 12 represents an electromechanical capping system for the nozzle arrangement of an aerosol generator suitable for use in the invention, FIG. 13 represents an optical liquid dose gauge suitable for use in the invention.

DETAILED DESCRIPTION

Figure 3:
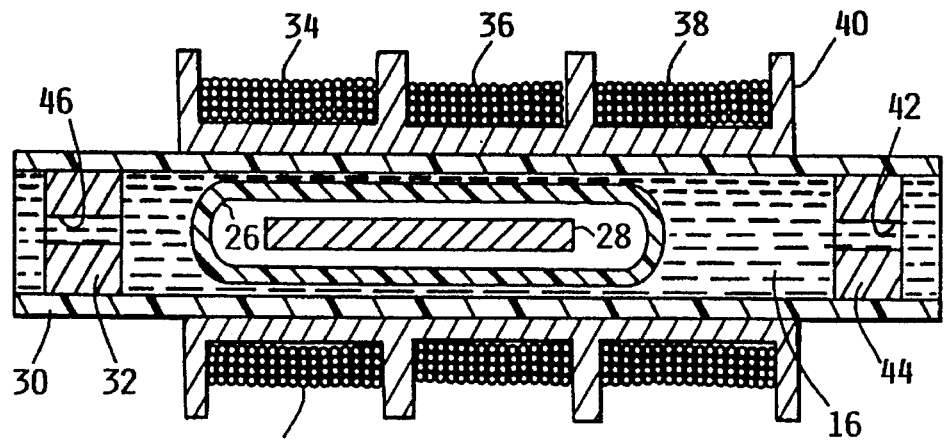
FIG. 3 is a cross-section diagram showing a metered liquid dose gauge, suitable for use in an inhaler of the invention.

Referring to FIG. 1a, the drug delivery system comprises a liquid reservoir (1), flow gauge (2) and aerosol generator (3) linked by tubing or channels or other means allowing the controlled flow of liquid between (1), (2) and (3). The flow gauge (2) and aerosol generator (3) are also connected to electronics (4) providing the necessary drive voltages and signal processing functions. A breath actuation sensor (5) is also linked to the electronics (4) and provides a trigger to start a metered dose delivery cycle. The liquid reservoir (1) and aerosol generator (3) are also provided with a vent valve and cap respectively, both of which are closed when the system is not in use. This system is a closed loop controlled drug delivery system.

An alternative system configuration is shown in FIG. 1b, comprising a liquid reservoir (6), aerosol generation (7), electronics (8) and a breath sensor (9). In this case where no flow gauge is included the delivered dose is controlled by the activation period of the aerosol generator alone and is therefore an open loop controlled drug delivery system.

The individual system components shown in FIGS. 1a and 1b will now be described.

Referring to FIG. 2, a reservoir for storing the liquid to be ejected with minimal evaporation losses and supplying the liquid at the correct pressure to the other system components, comprises an impermeable, solid vessel (12) containing a collapsible bag (10) filled with liquid (16). The bag (10) is filled with liquid so as not to contain any gas bubbles by a method such as vacuum back filling. The bag (10) is sealed to a filler tube (14) by tying, bonding or other such means at point (22). The stiffness and geometry of the bag walls is such that the bag tends to spring to a state of maximum internal volume, hence, as the liquid (16) is drawn from the reservoir then a negative differential pressure with respect to atmosphere is created. The pressure is typically of the order of a few centimeters head of water which is transmitted throughout the system and prevents seepage of liquid from the aerosol generator nozzles, whatever the orientation of the device. A piece of flexible soft tubing (20) in a material such as silicone rubber is attached to the filler tube (14) inside the bag to prevent damage to the bag if the device is subject to mechanical shocks. It also ensures that the liquid (16) is drawn from the centre of the bag (10) reducing the possibility of any unwanted bubbles incorporated due to imperfect filling being carried through the system. The vessel (12) also has a vent hole (18) which is linked to a valve at the end of the vent tube (24). This valve is opened to atmosphere when the device is in use to prevent an excessive negative pressure from building up in the reservoir as the liquid (16) is drawn from the bag (10).

Referring to FIG. 3 a liquid dose gauge comprises a length of tubing (30) in a suitable material such as glass or plastic which contains a free moving slug (26) in a suitable material or composite of materials such as glass, plastic or metal. The slug (26) contains a small piece of steel wire, ferrite or other magnetic material (28) which is fixed within the slug and serves to enable the slug (26) to be magnetically reset against an end stop (32) in the tube (30) when an end coil (34) is energised with electrical current.

The net density of the slug (26) is matched to that of the liquid (16) such that the operation of the flow gauge is independent of the unit orientation and motion. The slug (26) is restrained axially within a section of the tube (30) by the two end stops (32) and (44). These end stops each contain a central aperture (42) and (46) which allows the liquid (16) to flow through the gauge. The position of the slug (26) is monitored by an arrangement of three coils (34), (36) and (38) wound on a former (40), configured as a differential transformer. In this case, the central coil (36) is energised with an alternating current at a frequency of the order of 10 kHz. The mutual inductance between the central coil (36) and each of the outer coils (34) and (38) is dependent on the position of the magnetic material (28). If the coils (34) and (38) are connected in anti-phase then a null output is obtained when the magnetic material (28) is disposed symmetrically between the coils. Hence this is a convenient end point to detect for the travel of the slug (26) as the liquid (16) flows through the gauge. The general concept of the differential transformer is well known to those versed in the art of measurement systems. From the above it may be seen that the coil (34) and the magnetic material (28) perform dual functions, i.e., that of resetting the slug (28) against end stop (32) and that of enabling the detection of the end point. End point detection may also be achieved by using only a single coil (34), by monitoring the self inductance of that coil alone which will depend on the position of the magnetic material (28) within it. Typical dimensions for such a gauge may be approximately 10 mm in length with a tube bore of around 1 mm. A clearance of approximately 0.1 mm around the slug is suitable.

Figure 4A:
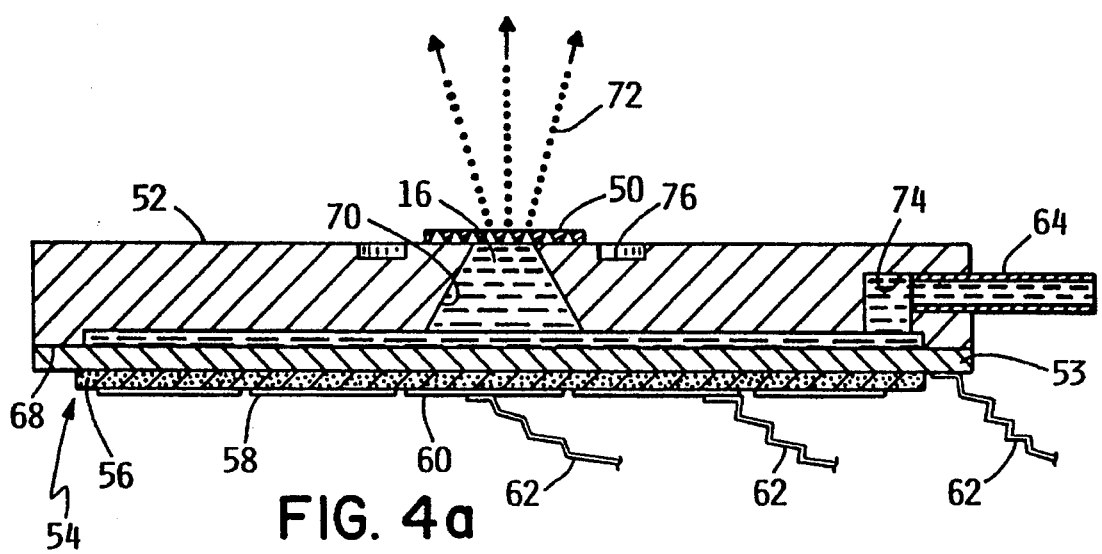
FIG. 4a is a cross-section diagram of an aerosol generator.
Figure 4B:
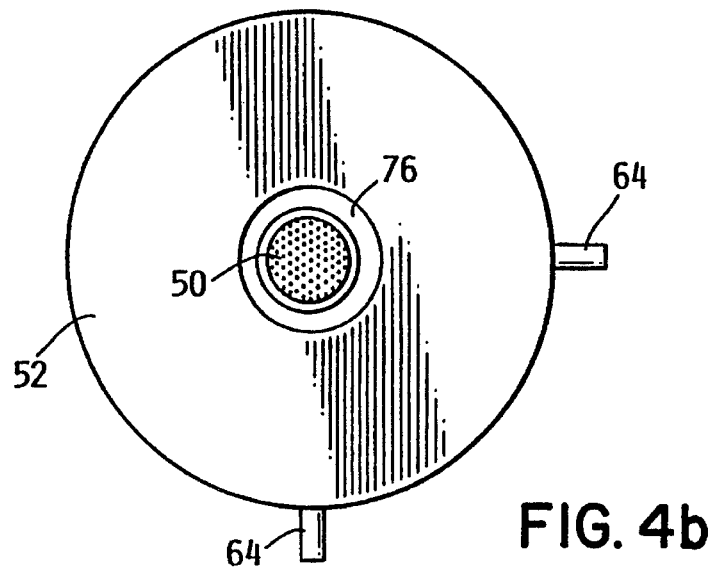
FIG. 4b is a front view of the aerosol generator of FIG. 4a, FIG. 5a is a cross-section through a silicon nozzle array, suitable for use in an inhaler of the invention.
Figure 5A:
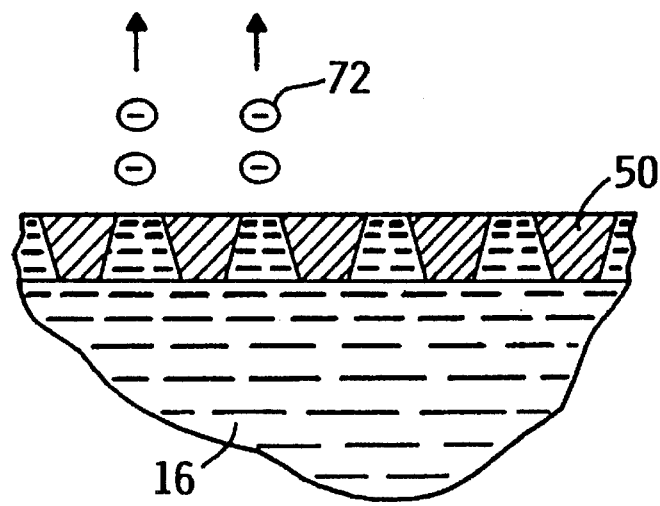
FIG. 5b depicts a cross-section through an electro formed nickel nozzle array, suitable for use in an inhaler of the invention.
Figure 5B:
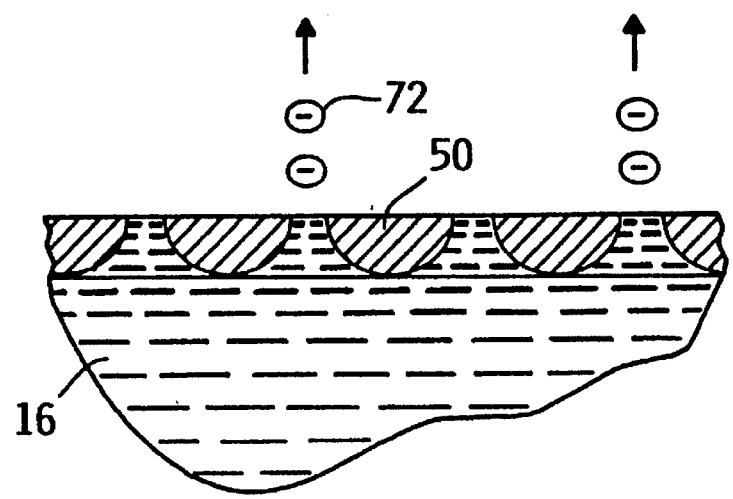

Referring to FIGS. 4a and 4b, an aerosol generator comprises a disc of material (52) such as aluminium alloy or plastics, e.g., Perspex, formed by machining, moulding or other shaping process to produce a central conical or exponentially shaped port (70), a mounting rim (68), filling ports (74) and a recessed groove (76). A vibrator element (54), such as those manufactured by Kyocera and Murata for audio sounders, is attached to the disc (52) around the mounting rim (68) by adhesive or bonding techniques. The vibrator element (54) comprises a brass disc electrode (53) about 0.2 m thick and 20 mm diameter onto which is bonded a smaller disc of piezo-electric material (56). One or more electrodes (58) and (60) are formed on the piezo-electric material (56) and lead wires (62) are connected to these electrodes and to disc electrode (53). When an electric field is applied between the electrodes, the vibrator element bends and may be excited into mechanical resonance by application of an alternating voltage at appropriate frequency. An array of nozzles (50) is attached over the narrow opening of the port (70) by adhesive or other bonding technique. The groove (76) prevents excessive spreading of adhesive over the disc surface where a cap may need to seal. The liquid to be ejected is introduced into the cavity formed by the disc (52), vibrator element (54) and nozzle array (50) by one or more feed tubes (64), sealed into the filling ports (74). When the vibrator element (54) is excited into a suitable resonance then ultrasonic vibrations are transferred into the liquid (16) and around the rim of the vibrator element into the disc (52) by motion of the vibrator element (54). These effects result in ultrasonic pressure pulses within the liquid (16) behind the nozzle array (50) and droplets (72) are formed as the liquid (16) is periodically ejected through the nozzle array (50) at ultrasonic frequencies. The optimum frequency of operation depends on the electromechanical properties of the vibrator element and on the fluid dynamics through the nozzles. With nozzle diameters in the range 5 to 10 μm, vibrator resonances in the range 100 to 250 kHz cause droplet emission from the device with modest electrical drive powers (<1 W). The resonances employed correspond to complex modes of vibration of the vibrator element (54) and are one or two orders of magnitude above the audible fundamental mode of vibration at which operation was intended by the manufacturers.

The central portions of the vibrator element (54) exhibit the highest amplitude of operation and the resulting pressure waves in the liquid (16) are concentrated by the tapered port (70) onto the nozzle array (50). In one embodiment, the overall size of the aerosol generator is approximately 20 mm in diameter and 3 mm thick. Efficient operation is observed with a conical central port tapering from 3 mm diameter to a 1 mm diameter droplet emitting area and a rim height of around 0.25 mm. Disc materials with both a low acoustic impedance and loss characteristics at the ultrasonic frequencies employed, e.g. aluminium alloy or Perspex were found to be the most suitable. If necessary all surfaces in contact with the liquid (16) may be coated with a protective layer, e.g. electroplated Ni or anodised to prevent corrosion.

The nozzle array (50) may be fabricated from an electroformed metal or metal alloy such as nickel or by anisotropic etching of a silicon wafer. FIGS. 5*a* and 5*b* depict a cross-section through part of a silicon nozzle array and an electroformed nickel nozzle array respectively. It is important for the efficient operation of the device for the nozzle to taper in leading up to the nozzle exit. The silicon nozzles show a linear profile whereas the electroformed nozzles show a curved profile, however, both geometries work effectively. The silicon nozzles may be fabricated by selective, anisotropic etching down the crystal planes of a double sided polished <100> silicon wafer. The etched nozzles were defined by photoresist and silicon oxide masks and etched in EDP solution. Such techniques are familiar to those versed in the art of silicon microfabrication techniques and are often used for producing thin diaphragms for pressure sensors. In either case, typically nozzle exit sizes are 5 to 10 μm and the nozzle plate thickness is typically around 20 to 100 μm.

The alternating voltage drive to the vibrator element (54) must be maintained at the correct frequency and amplitude to most efficiently excite the required resonance mode. It is common for audio vibrator elements to include a feedback electrode on the piezo layer which develops a potential when the vibrator element is flexed. Thus, the amplitude or phase or both of the signal from the feedback electrode relative to an oscillating drive signal voltage may be used to infer the mechanical behaviour of the vibrator element. Such a scheme is often used in the audio drive circuits for these vibrator elements. It is an aspect of this invention that the signal from a conventional audio feedback electrode may be used to control the drive electronics operating at ultrasonic frequencies, by locking the drive oscillator to a selected resonant mode. Manufacturing tolerances and the change in vibrator element (54) electromechanical properties when bonded to a disc (52) and placed in contact with a liquid (16) preclude accurate prediction of the required resonant frequency. The resonant peak may typically only be estimated to fall within a 10 to 20 kHz bandwidth.

With reference to FIG. 6*a*, a scheme for driving the vibrator element of the aerosol generator (84) at the correct frequency is illustrated by a functional block diagram. The vibrator element (54) is driven by a voltage controlled oscillator (VCO) (80) via a power output stage (82). The upper and lower frequency bounds of the VCO (80) may be precisely set to span a frequency range within which only the required resonance peak will lie. When the circuit is first energised the VCO (80) drives the vibrator element at the lower end of the frequency band. The amplitude of the signal from the vibrator element feedback electrode is derived by an envelope detector (demodulator) (86) and is compared against a preset threshold by the amplitude comparator (90). If the preset amplitude threshold is not exceeded i.e., the feedback signal is weak, then a ramp generator (92) continuously outputs a triangular voltage waveform against time to the VCO (80). As a result of this, the VCO (80) output frequency and hence the drive frequency to the vibrator element (84) is continually swept up and down between the fixed frequency bands of the VCO (80). If the feedback signal amplitude exceeds the preset threshold, i.e., the feedback signal is stronger indicating close proximity to the resonance peak, then an amplitude differentiator and comparator in (88) is used to determine whether the feedback signal is increasing or decreasing in magnitude. If it is found to be increasing then the voltage ramp direction remains unchanged, if it is steady or decreasing then the ramp direction is reversed. With this arrangement, a resonance peak is first located and then locked to by continuous 'hunting' about the peak response frequency.

With reference to FIG. 6*b*, a similar but simpler scheme for driving the vibrator element is described. Its mode of operation is similar to that of the system illustrated in FIG. 6*a* except that the amplitude threshold comparison is not made, but instead the signal amplitude is taken to be high enough all of the time, i.e., the frequency is always assumed to be in the vicinity of the required resonance peak. This latter system is preferable because of its reduced complexity but, it does require the resonant frequency to be more accurately predicted than is necessary for the former system described in FIG. 6*a*.

FIGS. 7*a*–7*f* show some example electronic circuits which may comprise the functional blocks illustrated in FIGS. 6*a* and 6*b*. The demodulator (86) comprises capacitors (700 and 703), diodes (701 and 702), resistor (704) and operational amplifier (op amp) (705). The alternating voltage signal from the vibrator element feedback element is input to the a.c. coupled demodulator (86) which gives a d.c. analogue output related to input signal amplitude. The amplitude comparator (90) comprises resistors (707 and 708), potentiometer (706) and comparator (709). If the signal from (86) exceeds the threshold set by (706) then the output signal level to (92) is 'high'. The comparator hysteresis is set by (707 and 708).

The amplitude differentiator and comparator (88) comprises resistors (710, 712,713, 716, 717, 718, 719 and 720), capacitors (711 and 715), operational amplifier (714) and comparator (721). The op-amp (714) and its associated components differentiate the amplitude signal from (86). The amplitude derivative is then thresholded by the comparator (721) and its associated components such that the output to (92) is 'low' when the signal from (86) is rising.

The ramp generator (92) comprises logic gates (722, 723, 724, 725, 726, 727, 728, 729 and 730), resistors (731, 732, 733,734 and 735), capacitor (736) and comparator (737). If the input level from (90) is 'low' then the output voltage to (80) will be a continuous triangular waveform oscillation. If the input level from (90) is 'high' then the output voltage to (80) will be a ramp waveform, which changes direction whenever the input level from (88) goes 'high'. If the latter remains 'low' then the ramp direction, whether it be up or down, remains unchanged.

The ramp voltage from (92) controls the VCO circuit (80) which comprises a VCO IC (741) together with resistors (738 and 739) and capacitor (740) which determine the upper and lower frequency limits of the VCO.

The output stages (82) comprise n-channel MOSFETS (742 and 743), resistors (748, 749 and 750), transistors (744, 745, 746 and 747), diodes (753 and 754), capacitors (751 and 752), inductor (755) and logic gate (756). Components (742, 748, 744,745, 751, 753,754 and 752) form a voltage doubler circuit to increase the supply voltage available to drive the vibrator element. components (756, 743,749, 746, 747,755 and 750) comprise a half bridge square drive circuit for the vibrator element. The inductor (755) and resistor (750) in combination with the vibrator element provide a matching output drive filter which affects the amplitude and frequency content of the vibrator element drive waveform, such that these may be set for optimum efficient operation.

Figure 8:
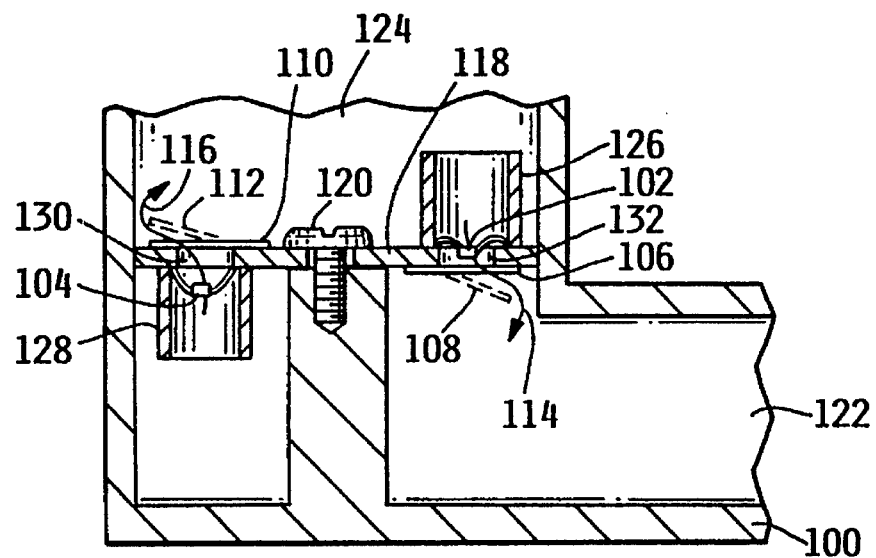
FIG. 8 depicts a cross-section through a breath actuation sensor, suitable for use in an inhaler of the invention.

With reference to FIG. 8, a breath actuation sensor comprises a pair of flap valves (110) and (106) covering apertures (130) and (132) respectively in a sheet of material (118). Behind flap valve (106) a thermistor (102) is situated in an inlet port (126). The sheet (118) is secured into a manifold (100) by a screw (120). Aperture (122) of the manifold (100) leads to a mouth piece whereas aperture (124) of the manifold (100) is open to atmosphere. As the patient inhales through the manifold, flap valve (106) opens to position (108) and air is drawn through the port (126) past the thermistor (102). The air flow is detected by its increased cooling effect on the thermistor (102) which is maintained at a temperature some 100° C. or so above ambient by the passage of an electrical current through it. The cooling effect on the thermistor is apparent by a change in the electrical resistance of the thermistor or by the electrical current required to maintain it at a constant temperature and resistance. Such techniques are well known to those versed in the art of 'hot wire' type anemometers. The flap valves (106) and (110) ensure that the predominant air flow (114) over the thermistor (102) is due to inhalation rather than expiration. Suitable electronics connected to the thermistor (102) can therefore generate a signal to trigger the aerosol delivery system when inhalation occurs through the manifold aperture (122). A second port (128) and thermistor (104) may be included if the exhaled air flow (116) is to be monitored. During expiration the flap valve (106) remains closed and the flap valve (110) assumes position (112) thus directing the air flow predominantly over thermistor (104).

Figure 9:
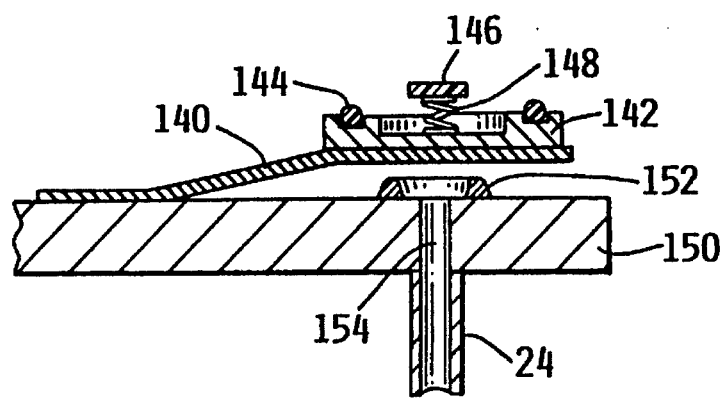
FIG. 9 is a schematic diagram of a cross-section through a nozzle cap and reservoir vent valve assembly, suitable for use in an inhaler of the invention.

With reference to FIG. 9, a sealing cap and reservoir vent valve assembly comprises a moveable member (150) onto which is attached a leaf spring (140) which carries a cap body (142). The cap body (142) seals against the front surface of the aerosol generator disc (52) outside of the groove (76) with a polymer 'o' ring (144). Just before the 'o' ring (144) seals the cap, a compliant polymer pad (146) contacts the nozzle array (50) and is held against it by a small spring (148). The purpose of the pad (146) is to effect a good mechanical seal against the nozzle array (50) which prevents air from being pushed in through the nozzle when the device is subjected to mechanical shocks. However, since the liquid (16) can be drawn by capillary action between the pad (146) and the nozzle array (50) to the edges of the pad (146), an outer 'o' ring seal (144) is also required to reduce evaporation losses from the system.

The vent port (18) from the reservoir is linked by tubing (24) and hole (154) to a vent valve comprising a compliant sealing ring (152) attached to the member (150) and the surface of the leaf spring (140). This arrangement is such that when a force on the member (150) is applied to seal the cap against the aerosol generator, the leaf spring (140) contacts the sealing ring (152) to close the vent valve. Hence, the entire system is then sealed off from the atmosphere and may be subjected to mechanical shocks and handling without bubbles being drawn into the system. It can, however, be advantageous to allow a small leak to atmosphere to occur in the vent tube (24) or seal between (140) and (152) such that the system internal pressure can equilibrate to atmosphere when changes in ambient temperature or pressure occur.

Figure 10:
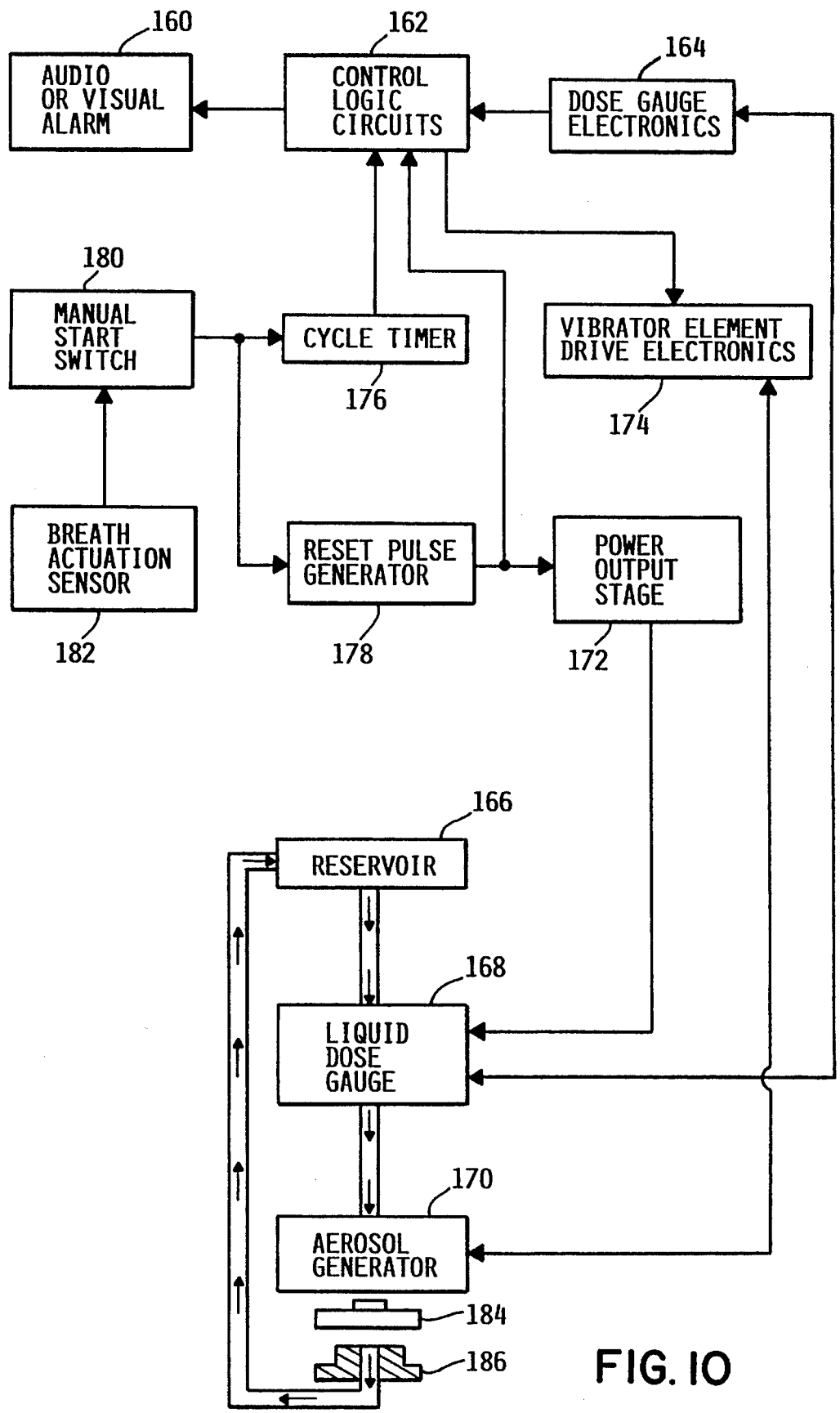
FIG. 10 is a function block diagram of a complete metered dose aerosol delivery system, suitable for use in an inhaler of the invention.

With reference to FIG. 10, a configuration of a complete electronic metered dose aerosol delivery system is illustrated by a function block diagram. Upon receiving a trigger signal from a manual start switch (180) or a breath actuation sensor (182), a cycle timer (176) is started and a reset pulse generator (178) activated. The reset pulse is amplified by a power output stage (172) and sent to the liquid dose gauge (168). The reset pulse generator (178) and cycle time (176) signals are input to control logic circuits (162) which energise the vibrator element drive electronics (174) when the reset pulse has finished but the cycle timer is still running. With the cap (184) removed from the aerosol generator (170) and the reservoir (166) vent valve (186) open, liquid flows from the reservoir (166) through the dosage gauge (168) and aerosol generator (170) when the vibrator element drive electronics (174) are energised. When the dose gauge (168) has reached its end point, a 'completed dose' signal is sent by the dose gauge electronics (164) to the control logic (162) which then deactivates the vibrator element drive electronics (174). Provided this occurs before the cycle timer (176) has timed out then the correct dose will have been delivered. If however, the 'completed dose' signal is not received before the cycle timer (176) times out then the control logic (162) generates an alarm signal indicating a failed dose delivery. This alarm signal activates an audio or visual alarm (160). One such possible audible alarm is to drive the vibrator element (54) with an audio frequency.

FIG. 11 shows a schematic diagram of an inhaler in accordance with the invention comprising a housing (204) defining a chamber for the aerosol generator (210) which is in communication with a mouthpiece (208). The medicament is held in reservoir (212) and may pass through conduits via dosage gauge (214) to the aerosol generator (210). Inhalation through the mouthpiece causes air flow through the air inlet (218), over the breath sensor and flap valve (216) and past the aerosol generator to the mouthpiece. On detection of the patient's inspiration a signal is received by the electronic control means (206) which activates the aerosol generator causing atomised droplets of liquid, represented by arrows (220) to be emitted into the air flow. The device is powered by battery (202). (A mouthpiece cap, vent valves and wiring have been omitted in the interests of clarity).

FIG. 12 is a schematic diagram of an electromechanical closure system combined with a droplet air mixer venturi in an inhaler having an aerosol generator of the type shown in FIGS. 4a and 4b. The aerosol generator (500) emits droplets into the throat of a venturi (502). The air flow through the venturi (502) throat is at right angles to the droplet emission direction and thorough mixing occurs before the exit flow (512).

The nozzle cover (504) is attached to a carrier (506) which has an internal thread (510). The carrier (506) and cover (504) are moved linearly by a leadscrew (508), which matches the thread (510), and a motor (516). The motor (516) is driven by a bipolar electrical supply (514) which can reverse the motor direction to move the cover on or off. When the cover is removed the carrier rests in the position (520) against a mechanical stop (518) marked in FIG. 12 with the cover flush with the venturi throat wall, allowing the air flow to be almost undisturbed.

FIG. 13 represents an alternative liquid dose gauge to that shown in FIG. 3.

The liquid dose gauge comprises a tube or channel (418) containing a measurement slug (424) with approximately neutral buoyancy in the liquid (416). At the start of the measurement cycle, the measurement slug (424) is reset against an end stop (422) by means of a magnetic slug (406) and a moving external magnet or magnetic field (not shown). The magnetic slug (406) is then returned against the end stop (420). A light source (408) such as a light emitting diode projects light through a pair of apertures (412 and 414) onto a photodiode (410). As the liquid (416) flows through the device, the measurement slug (424) moves along to position (425) whereupon the slug (424) blocks out about half of the light passing through the apertures (412 and 414) onto the photodiode (410). Electronics connected to the photodiode (410) detects this optical signal change and indicates that the liquid (416) dose has been delivered.

Figure 14A:
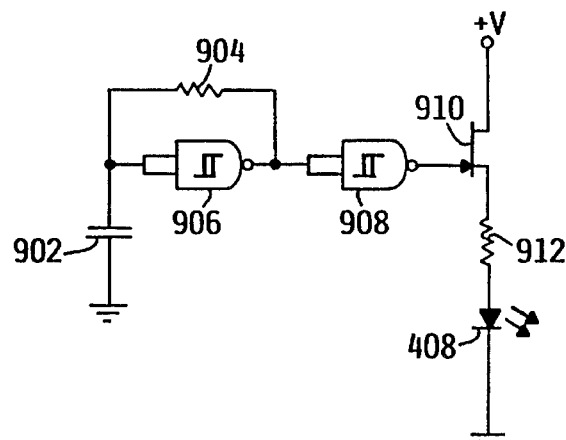
FIGS. 14a–14c represent electronic circuits suitable to interface with the dose gauge of FIG. 13, FIGS. 15(a), 15(b) and 15(c) represent end, side and plan views of a further inhaler in accordance with the invention.
Figure 14B:
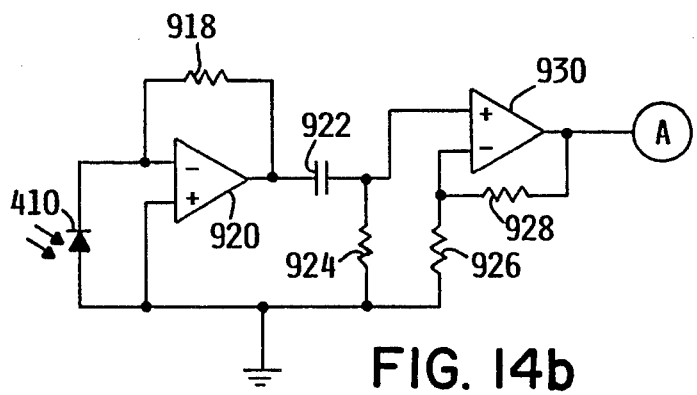
Figure 14C:
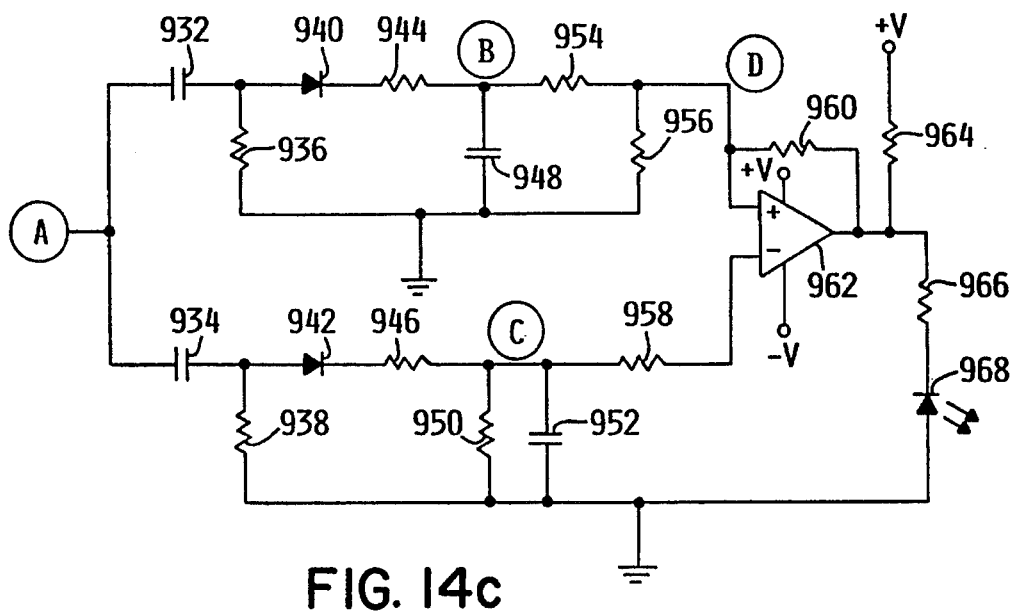

With reference to FIGS. 14a–14c, electronic circuits to interface to the dose gauge of FIG. 13 are illustrated. The light emitting diode (LED) (408) is driven by oscillator components (902, 904, 906 and 908) and driver components (910 and 912). The drive frequency is typically around 1 to 10 kHz and enables the optical receiver to distinguish the signal from any background light.

Photodiode (410) is connected to a transimpedance amplifier circuit (918 and 920) and is a.c. coupled to pass the modulation into an amplifier circuit (922, 924, 926, 928 and 930). Point A therefore carries an amplitude modulated signal. When the measurement slug (424) in FIG. 13 does not obscure the apertures (412 and 414) then a steady state a.c. signal is present at point A. A demodulation circuit with a time constant of around 0.1 to 1 second (932, 936, 940, 944, 948, 954 and 956) generates a d.c. voltage at point B related to the signal amplitude. A second parallel demodulator circuit with a shorter time constant of around 1 to 10 milliseconds (934, 938, 942, 946, 950, 952 and 958) generates a d.c. voltage at point C. The voltage at point B is potentially divided by a factor of around 2 and compared to the voltage on point C by a comparator circuit (962, 960 and 964). State indication of the comparator is achieved by driving an LED (968) through a resistor (966). In the steady state with light passing across the gauge, the comparator drives the LED (968) on. When the apertures (412) and (414) shown in FIG. 13 are partially obscured, i.e., about half-way across, by the slug (424) as it moves, then the transient change in signal amplitude at point A is followed by the faster demodulator (but not by the slower one). Hence, the voltage at point C dips below that at point D (which is about half that at point B) and the comparator state changes, extinguishing the drive to the LED (968). Hysteresis provided by resistors (954, 956 and 960) maintains the comparator state until the optical signal magnitude increases when the slug (424) is reset.

FIGS. 15 to 19 illustrate an inhaler in accordance with the invention having a reusable hand unit and replaceable cartridge.

Figure 15C:
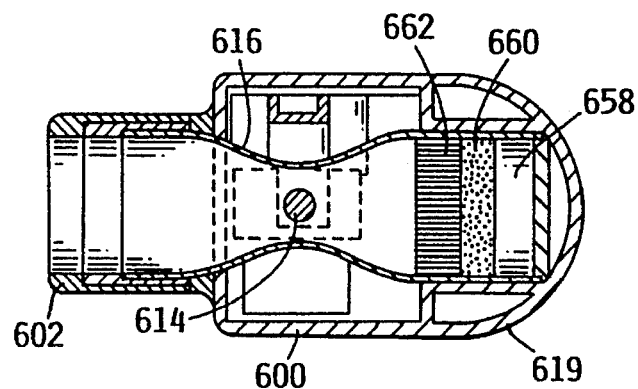
Figures 15A, 15B:
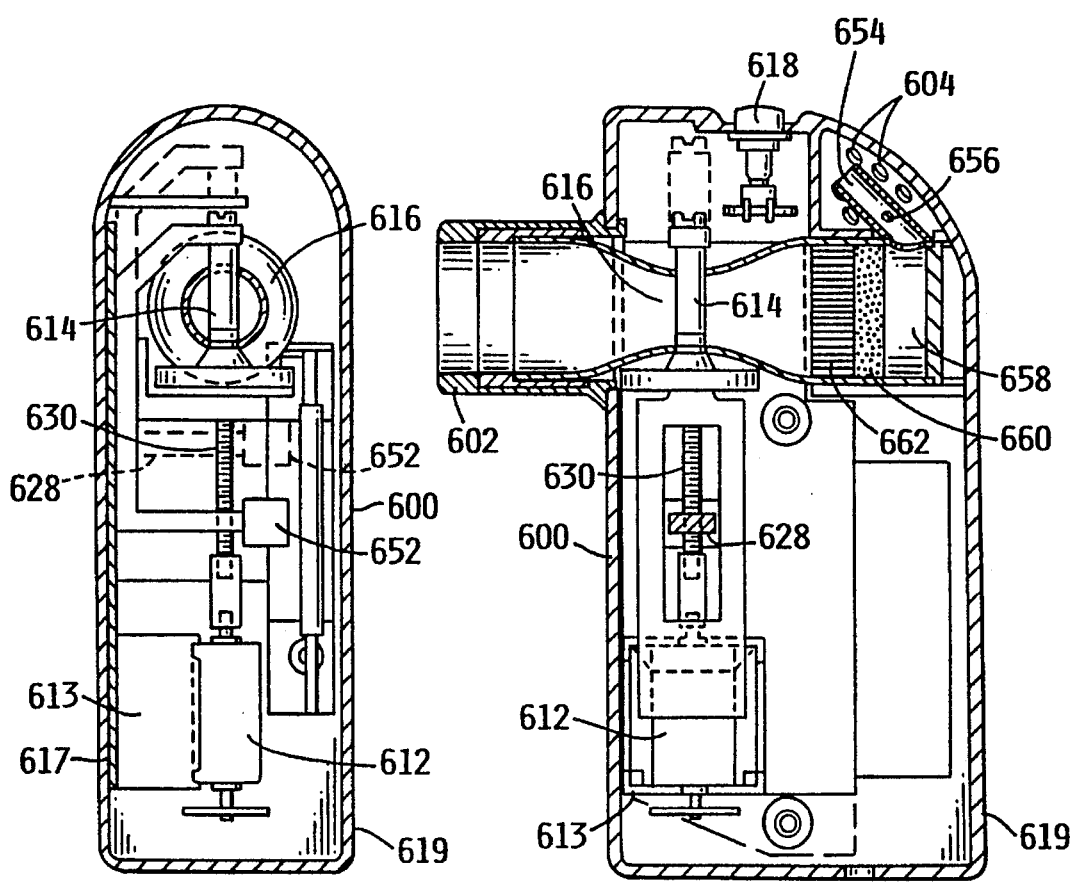
Figure 16:
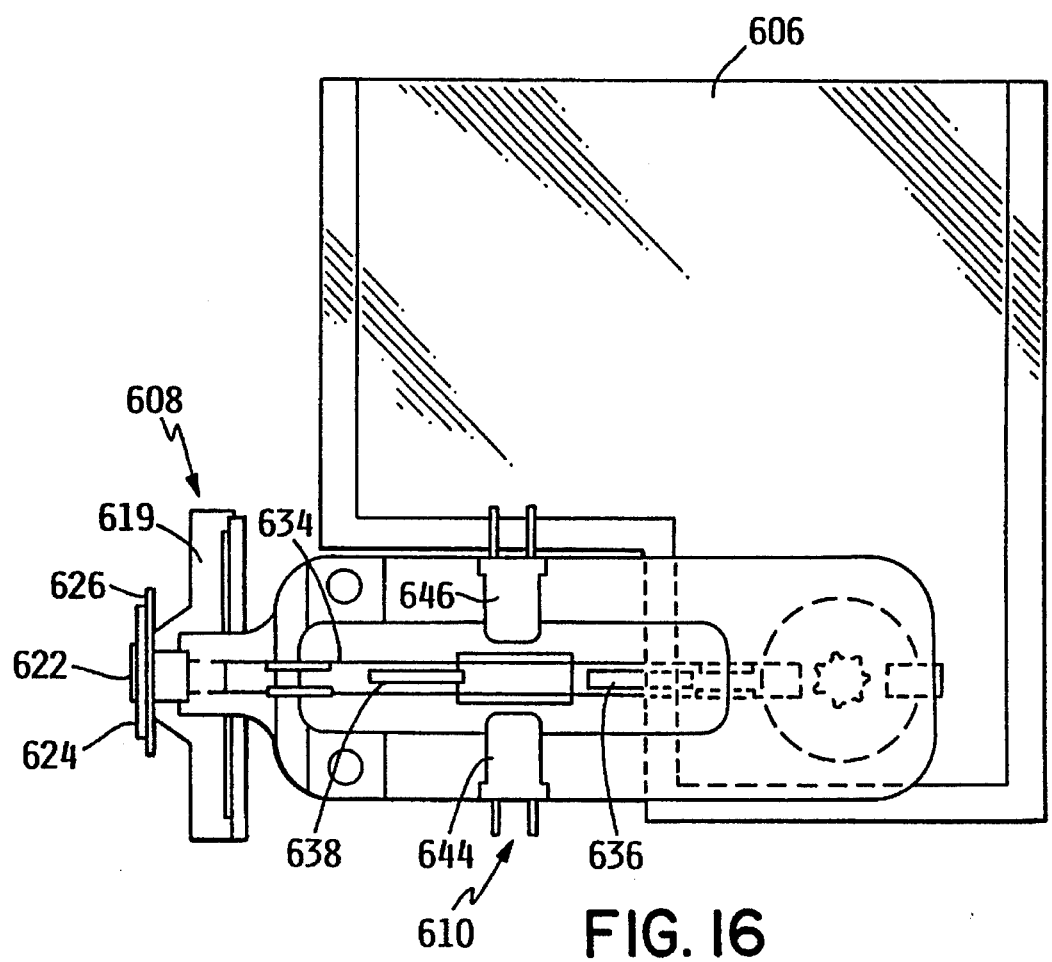
FIGS. 16 and 17 represent diagrammatic plan and side views of a replaceable cartridge for use in the inhaler of FIG. 15.
Figure 17:
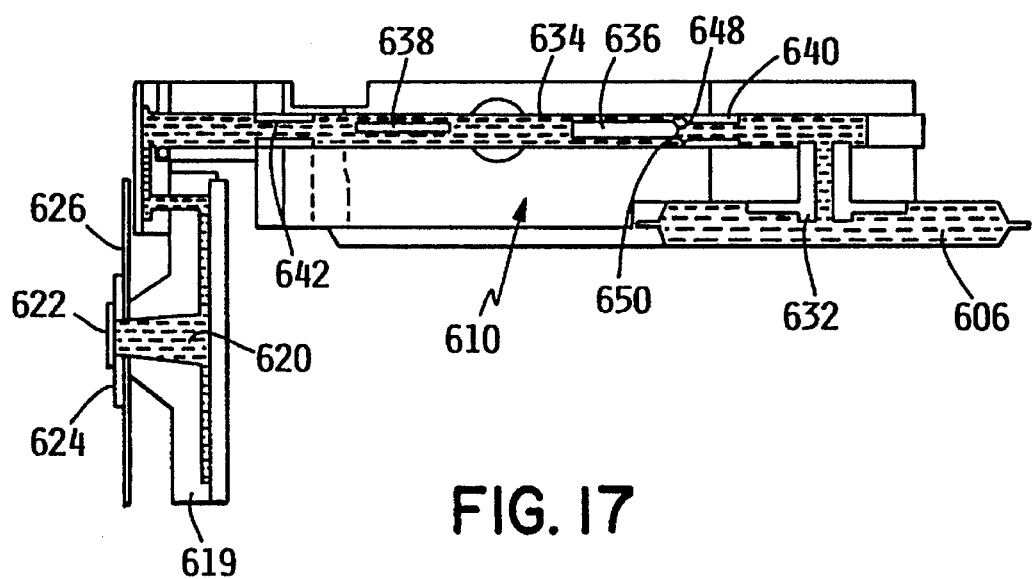

FIGS. 15a, b and c represent end side and plan views showing the components of the inhaler with the cartridge in place. The inhaler comprises a housing (600) having a mouthpiece (602) and air inlet ports (604). The housing contains a replaceable cartridge, details of which are shown in FIGS. 16 and 17, comprising a reservoir (606) an aerosol generator (608) and dose gauge (610). As seen in FIGS. 16 and 17, reservoir (606), aerosol generator (608), and dose gauge (610), are formed as a single integral unit. In addition, as seen for example in FIG. 17, a continuous passageway is formed between reservoir (606) and aerosol generator (608) so as to allow for a continuous stream of liquid medicament between the reservoir and the aerosol generator. The housing also encloses the reusable components of the inhaler including the motor (612), the cap (614) for the aerosol generator and the venturi (616).

Figure 18:
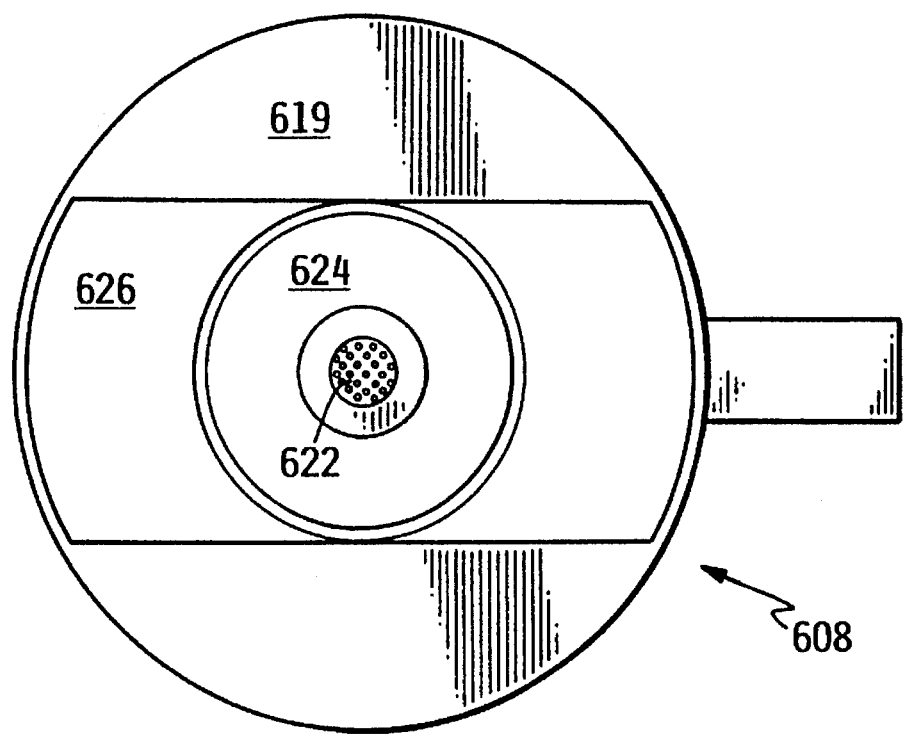
FIG. 18 represents a diagram of the aerosol generator used in the inhaler of FIGS. 15 to 17.

The aerosol generator (608) is shown in detail in FIGS. 16, 17 and 18. The generator comprises a housing (618) defining a chamber (620) having at one end a nozzle array (622). The chamber is in communication with a reservoir (606) via a dosage gauge (610). A vibrator element comprising a piezo-electric ring (624) mounted on a metal disc (626) is attached in close proximity to the nozzle array (622) such that ultrasonic energy from the vibrator element is transferred directly to the nozzle array. The metal disc (626) is shaped (see FIG. 18) such that it may be accommodated in the curve of the venturi (616) (see FIG. 15b). The diameter of the metal disc is preferably about 20 mm and it is attached over a central portion of about 4 mm diameter. The vibrator element is preferably driven at high frequency e.g. 250 to 400 kHz to provide a good flow rate through the aerosol generator and to reduce the effect of bubble formation.

Figure 19:
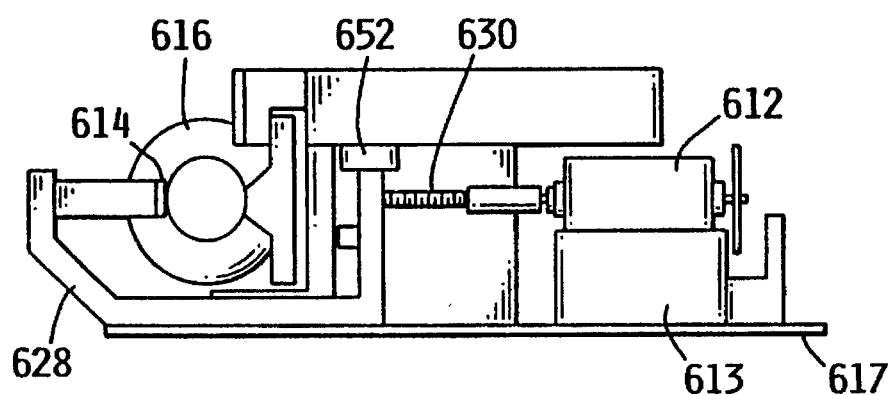
FIG. 19 represents a diagram of the cap arrangement used in the inhaler of FIG. 15.

The aerosol generator is sealed by a cap (614) when not in use (see FIG. 15a). The cap is carried on a slider which is moved by a lead screw (630) driven by motor (612). The motor (612) is mounted on a block (613) secured to base plate (615). When the inhaler is switched on by switch (618) the motor is activated causing the slider (628) to be moved displacing the cap (614) away from the aerosol generator (608) as shown in FIG. 19 and in dotted outline in FIG. 15a.

Figure 6A:
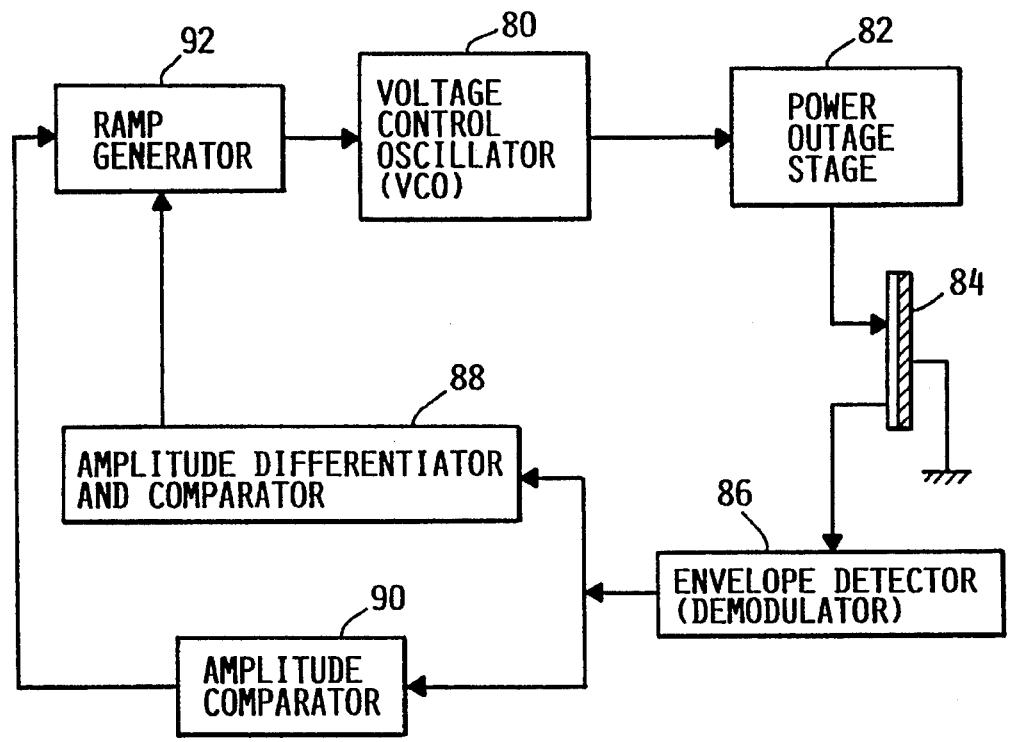
FIGS. 6a and 6b are function block diagrams of electronic circuits for maintaining the vibrator element at a selected resonant frequency.
Figure 6B:
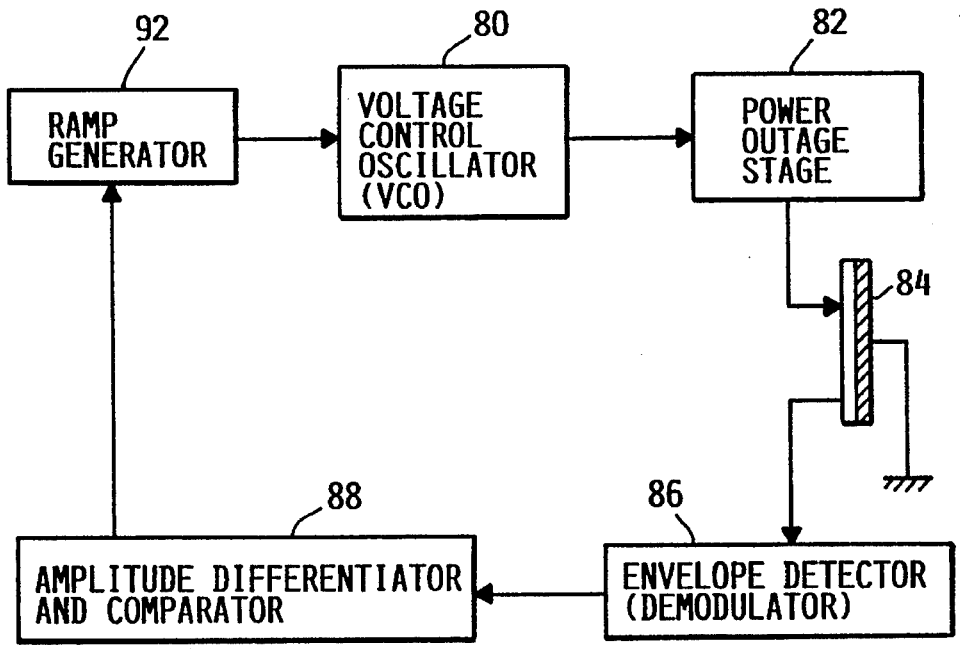
Figure 7A:
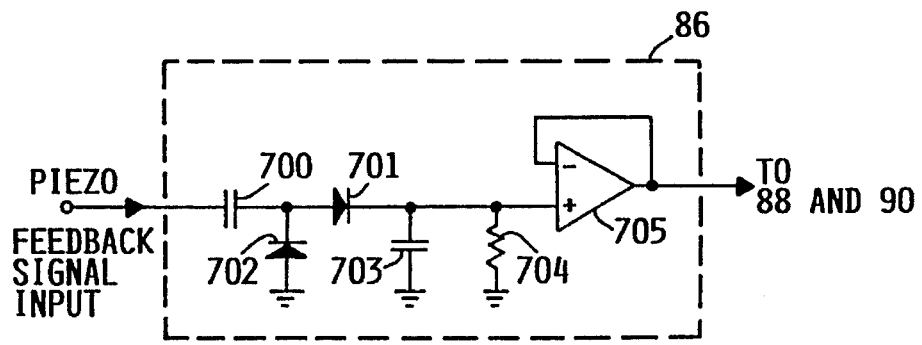
FIGS. 7a–7f show sample electronic circuits for the blocks of FIGS. 6a and 6b.
Figure 7B:
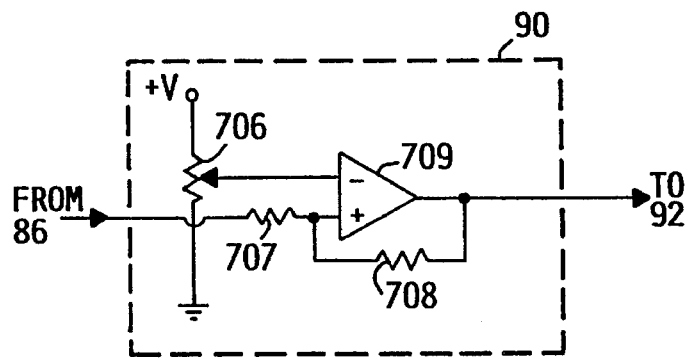
Figure 7C:
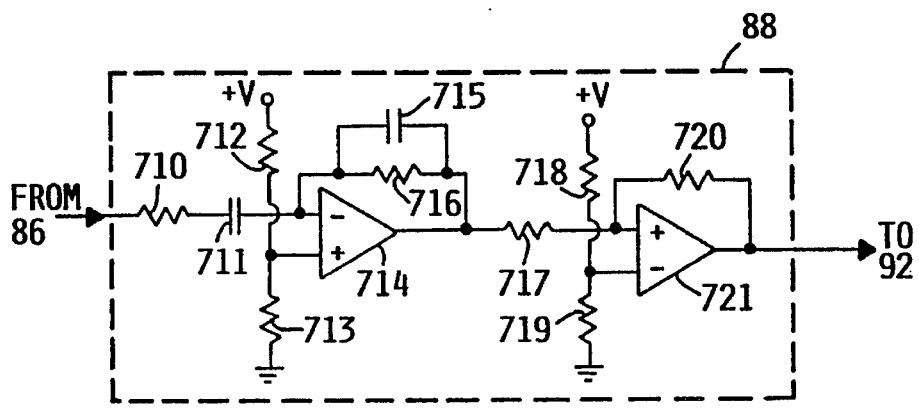
Figure 7D:
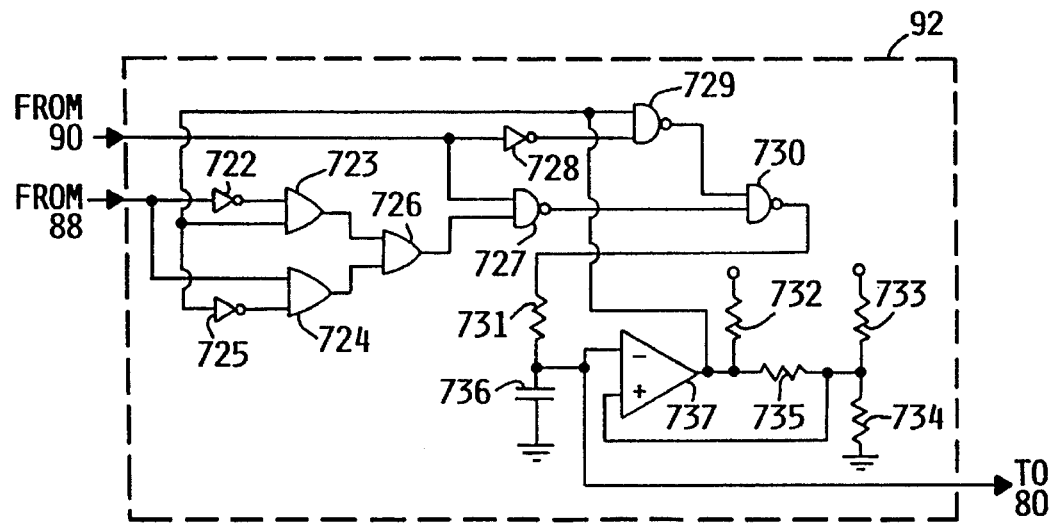
Figure 7E:
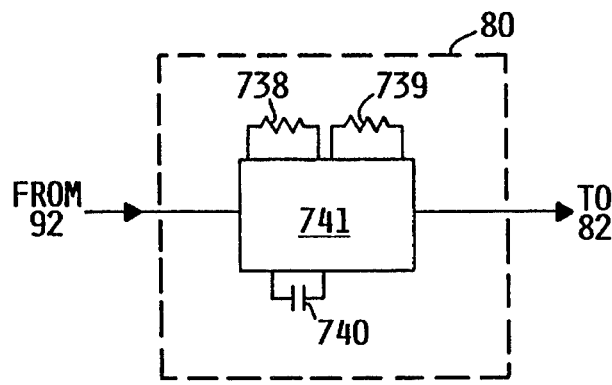
Figure 7F:
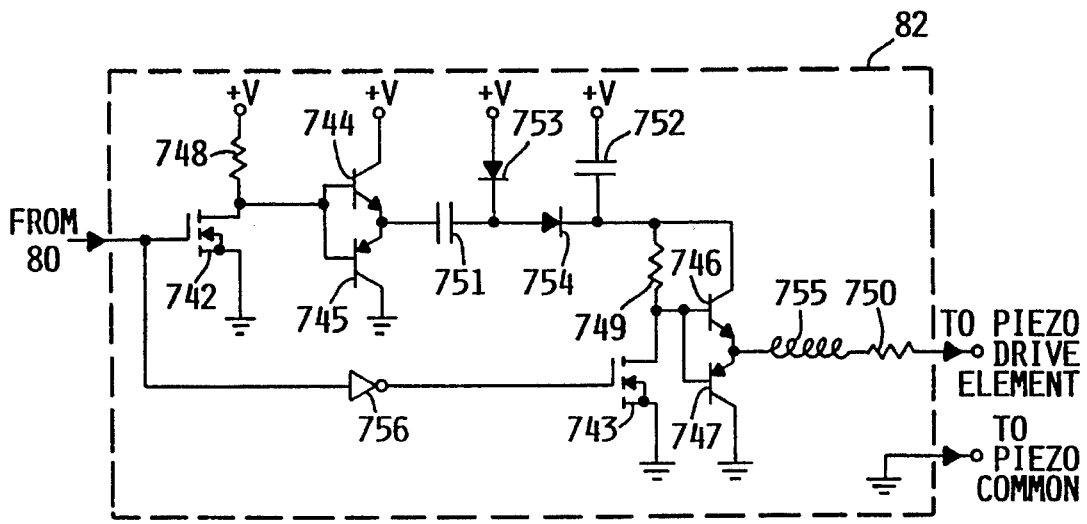

The dosage gauge (610) is positioned between the reservoir (606) and the aerosol generator (608). The reservoir (606) comprises a sachet which is heat sealed around its margins and comprises a connector (632) to provide a liquid communication with the dose gauge (610). The dose gauge comprises a tube (634) containing a neutral buoyancy measurement slug (636), a magnetic reset slug (638) an upstream end stop (640) and a downstream stop (642). The detection means for the slug (636) comprises a light emitting diode (644) and a photodiode (646). The slug (636) is conveniently provided with a shaped end (648) e.g. hemispherical, which may be held in sealing engagement with a corresponding shaped surface (650) at the end of the upstream stop (640) to provide a valve preventing liquid flow. The slug (636) is held against the stop (640) by moving the magnetic slug (638) upstream and holding the magnetic slug in that position. Movement of the magnetic slug (638) is accomplished by magnet (652) mounted on the slider (628) of the cap. Thus, when the cap (614) is in the closed position the magnetic slug (638) will be moved to its upstream position holding the slug (636) against the upstream stop (640), thereby acting as a closed valve. When the cap (614) is moved to its opened position the magnet (652) will be moved with the slider (628) causing movement of the magnetic slug to its downstream position, thereby allowing movement of the slug (636) when the aerosol generator is operated. Operation of the aerosol generator causes dispensing of the liquid medicament and movement of the slug (636) downstream to be detected by the detection system comprising the light emitting diode and photo-diode. The detection system may be of the digital type i.e. providing dose not completed and dose completed outputs only to switch off the aerosol generator when a dose has been administered, or it can be of the analogue type to give a continuous reading of volume dispensed from which the instantaneous flow rate can be derived for frequency tuning of the aerosol generator. For example, the frequency scanning referred to with respect to FIG. 6a could be used to locate a vibrator element drive frequency which gives a flow rate exceeding a pre-determined flow rate threshold. The analogue dose gauge may utilise a larger area light source and detector such that the received signal will vary according to the position of the slug (636).

The venturi (616) performs the function of mixing the liquid droplets emitted by the aerosol generator with an orthogonal air stream before the droplets have a chance to collide with each other too many times. The droplet size is very important in the delivery of drug to the respiratory system of the patient and repeated collision of droplets can result in the formation of large droplets which are too large to be inhaled properly. As the patient breathes through the mouthpiece (602) air passes through the inlet holes (604) in the housing and through inlet port (654) (FIG. 15b) into the venturi. A thermistor (656) is positioned within the port (654) to detect the incoming air flow and provide a signal which actuates the aerosol generator. The incoming air to the venturi is distributed over the whole venturi inlet by the provision of air buffer space (658) and foam disc (660) which is an open cell foam providing some resistance to the incoming air flow so that the air flow from the foam pad is substantially the same in all regions and is independent of the turbulence of the incoming airstream. Air from the foam buffer passes through a honeycomb of tubes (662) to remove any translational turbulence in the airstream and to ensure the air flow across the nozzle array is laminer. The tubes preferably have an internal diameter of 0.5 to 1 mm and a length of about 5 mm. The honeycomb may conveniently be constructed from corrugated foil coiled into a spiral. The air flow from the honeycomb tubes is an even laminar flow and the venturi gradually closes down increasing the air velocity for mixing with the droplets from the aerosol generator at the venturi throat. Thereafter, the venturi expands and the velocity of the air flow and entrained droplets is reduced before reaching the mouthpiece. In order to maintain a slight negative pressure in the reservoir it may be desirable to provide a conduit or passage connecting the venturi to the region of the reservoir in view of the low pressure in the venturi during inhalation.

Figure 20A:
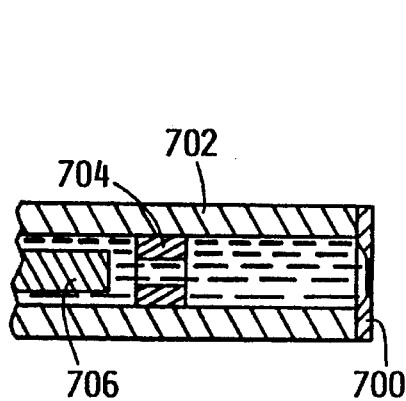
FIGS. 20(a) to 20(d) represents a diagram showing alternative configurations of an aerosol generator having a replaceable cartridge.
Figures 20B, 20C:
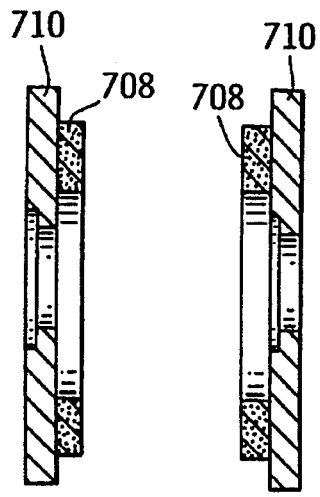

It is not essential for the vibrating element to be present in the replaceable cartridge and it is possible to incorporate this component into the re-usable unit. FIG. 20 of the accompanying drawings illustrates different configurations by which a nozzle array (FIG. 20a) may be located within a vibrating element (FIGS. 20b, c and d) to form an aerosol generator.

Figure 20D:
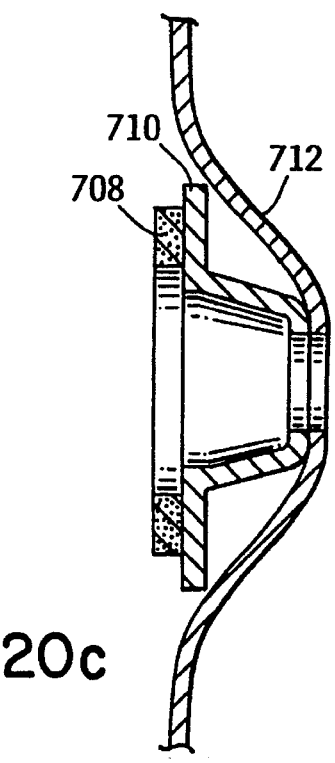

FIG. 20a shows a nozzle array (700) positioned at the end of a straight section tube (702) which forms the tube of a dosage gauge and cavity. The dose gauge end stop (704) and a portion of the magnetic slug (706) are shown. Different configurations of vibrating element comprising a piezo-electric ring (708) and metal disc (710) are shown in FIGS. 20b, c and d. The arrangements of FIGS. 20b and c differ in the position of the piezo-electric ring (708). FIG. 20d illustrates a shaped metal disc (710) which facilitates fitment into the throat of the venturi (712).

It has been found that efficient aerosol generation is achieved if the nozzle arrangement and vibrating element are constructed and arranged to ensure radial transfer of energy. Thus, it is preferred that the nozzle array (700) and/or tube (702) is a tight fit within the disc (710) in order to optimise the transfer of ultrasonic energy between the vibrating element and nozzle array. This may be achieved by the arrangement as illustrated in FIG. 20, although other configurations are readily possible, for example, the end of the tube (702) may be provided with a conical surface which fits within a complementary aperture on the metal disc.

The aerosol generator may comprise means other than a piezo-electric element to generate the necessary vibrations. The emergence of magnetostrictive materials, such as, Terfenol D in recent years allows the use of such materials as a driving element. Whilst the present cost of these materials is higher than that of piezo-electric elements, the energy density is higher and equivalent power actuators can be made with less material. Such actuators are electro-magnetically excited and the coil turns may be tailored to suit a given drive voltage such as the battery voltage, without need for additional inductors or transformers which the higher voltage piezo-electric elements may require.

Figure 21:
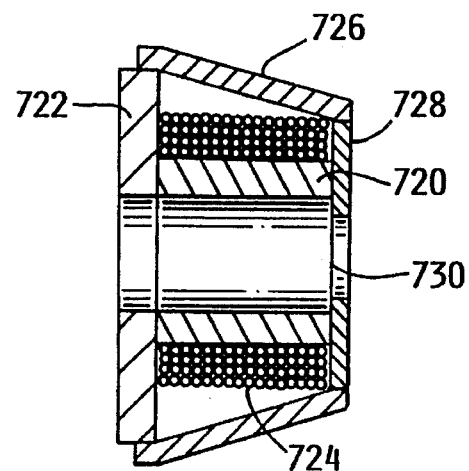
FIG. 21 represents a diagram of a magnetostrictive drive for use in an inhaler of the invention.

FIG. 21 of the accompanying drawings illustrates a nozzle arrangement having a magnetostrictive actuating element. The arrangement comprises a magnetorestrictive tube (720) magnetically biased by a permanent magnet (722) and excited by windings (724) forming an electro magnet. The pole pieces (726, 728) confine the flux within the tube (720). An alternating current in the windings (724) induces an alternating flux in the magnetorestrictive tube (720) which causes it to change its length. Thus, pole piece (728) moves in an oscillating manner with respect to the magnet (722). A tube and nozzle array as illustrated in FIG. 20a may be pushed into the magnetostrictive tube (720) such that the nozzle array is pushed against the face (730) of the pole piece (728) so that vibrations from the motion of pole piece (728) are transferred to the nozzle array.

We claim:

1. An inhaler device for dispensing droplets of liquid medicament to a patient comprising a body having a mouthpiece or nasal adaptor, a reservoir of liquid medicament, and an aerosol generator in communication with said reservoir, the aerosol generator comprising a chamber for liquid medicament and a nozzle arrangement comprising a plurality of orifices in fluid flow relationship with liquid medicament in said chamber, the reservoir having walls which tend to spring to a state of maximum internal volume so as to create a slight negative head of pressure within said reservoir and said chamber, the aerosol generator further comprising means for cyclically pressurising the liquid medicament in said chamber such that liquid from said chamber is periodically expelled through the orifices as atomised droplets of liquid medicament so they may be inhaled via the mouthpiece or nasal adaptor, the inhaler device additionally comprising dosage control means for deactivating the aerosol generator after a predetermined time or after a predetermined volume of liquid medicament has been expelled from the chamber.

2. An inhaler device as claimed in claim 1 wherein the means for cyclically pressurising the liquid medicament comprises a wall opposite the nozzle arrangement comprising a flexible portion attached to a piezo-electric element such that excitation of the piezo-electric element causes vibration of the flexible portion resulting in cyclic pressurisation of the liquid medicament in the chamber.

3. An inhaler device as claimed in claim 2 comprising means to excite the piezo-electric element at a resonant frequency within the frequency range of about 10 to 500 kHz.

4. An inhaler device as claimed in claim 2 further comprising means to excite the piezo-electric element at a resonant frequency within the frequency range of about 100 to 250 kHz.

5. An inhaler device as claimed in claim 2 further comprising means to excite the piezo-electric element at a resonant frequency within the frequency range of about 50 to 250 kHz.

6. An inhaler device as claimed in claim 1 wherein the nozzle arrangement is flexible and the means for cyclically pressurising the liquid medicament comprises a piezo-electric element associated with the flexible nozzle arrangement such that excitation of the piezo-electric element causes vibration of the nozzle arrangement resulting in cyclic pressurisation of the liquid medicament in the chamber.

7. An inhaler device as claimed in claim 6 wherein the piezo-electric element is in the form off a ring secured to a metal disc, the ring and metal disc each having a central opening to accommodate attachment of the piezo-electric element to the aerosol generator adjacent the nozzle arrangement.

8. An inhaler device as claimed in claim 7 further comprising means to excite the piezo-electric element at a resonant frequency within the frequency range of about 250 to 400 kHz.

9. An inhaler device as claimed in claim 6 further comprising means to excite the piezo-electric element at a resonant frequency within the frequency range of about 250 to 400 kHz.

10. An inhaler device as claimed in claim 1 wherein the reservoir is in the form of a collapsible bag.

11. An inhaler device as claimed in claim 1 wherein the dosage control means comprises means for measuring the volume of liquid supplied to the chamber, means for generating a signal after a predetermined volume of liquid has been measured, and means for deactivating the aerosol generator upon the generation of said signal.

12. An inhaler device as claimed in claim 11 further comprising a conduit connecting the reservoir and the chamber, the volume measuring means comprising a close fitting, free moving slug positioned in said conduit and having a density matched to that of the liquid medicament and means for detecting the position of the slug comprising optical, mechanical, or electromagnetic detection means.

13. An inhaler device as claimed in claim 12 in which the volume measuring means additionally comprises two stops for limiting movement of the slug therebetween and means for setting the slug against the upstream stop.

14. An inhaler device as claimed in claim 12 wherein the detecting means comprises means for continuously detecting the position of the slug and said signal generating means is capable of providing a signal representative of the instantaneous flow rate.

15. An inhaler device as claimed in claim 14 wherein said means for cyclically pressurising the liquid medicament comprises a piezo-electric element which vibrates said aerosol generator when excited, said inhaler device further comprising means for modulating the excitation of said piezo-electric element in accordance with said signal.

16. An inhaler device as claimed in claim 1 further comprising a breath actuation sensor for detecting a patient's inspiration through the mouthpiece or nasal adaptor and means for actuating the aerosol generator when inspiration is detected.

17. An inhaler device as claimed in claim 16 in which the breath actuation sensor comprises a pivoted vane, a flow transducer, a pressure differential transducer or a temperature sensor.

18. An inhaler device as claimed in claim 1 further comprising means for removing gas bubbles from the liquid medicament comprising a microporous material having one surface in contact with the liquid medicament and an opposite surface exposed to a region of low pressure or vacuum.

19. An inhaler device as claimed in claim 1 further comprising a venturi in communication with the mouthpiece or nasal adaptor such that the atomized droplets are directed into and substantially at right angles to the air flow generated through the venturi during inhalation through the mouthpiece or nasal adaptor.

20. An inhaler device as claimed in claim 1 wherein the inhaler device is configured as a reusable hand unit with a replaceable cartridge, said replaceable cartridge including the aerosol generator, including the nozzle arrangement and the chamber, and the reservoir as a single integral unit, a continuous passageway being formed between said reservoir and said aerosol generator so as to allow for a continuous stream of liquid medicament between said reservoir and said aerosol generator.

21. An inhaler device for dispensing droplets of liquid medicament to a patient comprising a body having a mouthpiece or nasal adaptor, a reservoir of liquid medicament, and an aerosol generator in communication with said reservoir, the aerosol generator comprising a chamber for liquid medicament and a nozzle arrangement comprising a plurality of orifices in fluid flow relationship with liquid medicament in said chamber, the aerosol generator further comprising means for cyclically pressurising the liquid medicament in said chamber such that liquid from said chamber is periodically expelled through the orifices as atomised droplets of liquid medicament so they may be inhaled via the mouthpiece or nasal adaptor, the inhaler device additionally comprising dosage control means for deactivating the aerosol generator after a predetermined time or after a predetermined volume of liquid medicament has been expelled from the chamber, the inhaler device further comprising means for removing gas bubbles from the liquid medicament comprising a microporous material having one surface in contact with the liquid medicament and an opposite surface exposed to a region of low pressure or vacuum.

22. An inhaler device as claimed in claim 21 wherein the inhaler device is configured as a reusable hand unit with a replaceable cartridge, said replaceable cartridge including the aerosol generator, including the nozzle arrangement and the chamber, and the reservoir as a single integral unit, a continuous passageway being formed between said reservoir and said aerosol generator so as to allow for a continuous stream of liquid medicament between said reservoir and said aerosol generator.

23. An inhaler device as claimed in claim 21 wherein the nozzle arrangement is flexible and the means for cyclically pressurising the liquid medicament comprises a piezo-electric element associated with the flexible nozzle arrangement such that excitation of the piezo-electric element causes vibration of the nozzle arrangement resulting in cyclic pressurisation of the liquid medicament in the chamber.

24. An inhaler device as claimed in claim 23 wherein the piezo-electric element is in the form of a ring secured to a metal disc, the ring and metal disc each having a central opening to accommodate attachment of the piezo-electric element to the aerosol generator adjacent the nozzle arrangement.

* * * * *

UNITED STATES PATENT AND TRADEMARK OFFICE
CERTIFICATE OF CORRECTION

PATENT NO.: 5,487,378

DATED: January 30, 1996

INVENTOR(S): Paul A. Robertson et al.

It is certified that error appears in the above-identified patent and that said Letters Patent is hereby corrected as shown below:

Item [57], in the Abstract, line 10, "atomizer" should be —atomized—

Col. 19, line 13, claim 7, line 2, "off" should be —of—.

Signed and Sealed this

Twenty-first Day of May, 1996

Attest:

BRUCE LEHMAN

Attesting Officer

Commissioner of Patents and Trademarks